(12) United States Patent
Kim et al.

(10) Patent No.: US 11,689,840 B2
(45) Date of Patent: Jun. 27, 2023

(54) AUDIO OUTPUT DEVICE FOR OBTAINING BIOMETRIC DATA AND METHOD OF OPERATING SAME

(71) Applicant: Samsung Electronics Co., Ltd., Suwon-si (KR)

(72) Inventors: Jungmo Kim, Suwon-si (KR); Minho Park, Suwon-si (KR); Daehyeong Lim, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 46 days.

(21) Appl. No.: 17/338,904

(22) Filed: Jun. 4, 2021

(65) Prior Publication Data
US 2021/0385567 A1    Dec. 9, 2021

(30) Foreign Application Priority Data

Jun. 5, 2020  (KR) .......................... 10-2020-0068584

(51) Int. Cl.
*H04R 1/10*      (2006.01)
*G06F 21/32*     (2013.01)
(Continued)

(52) U.S. Cl.
CPC ........... *H04R 1/1041* (2013.01); *G06F 21/32* (2013.01); *H04R 1/1091* (2013.01);
(Continued)

(58) Field of Classification Search
CPC ................ H04R 1/1041; H04R 1/1091; H04R 2201/105; H04R 1/1016; H04R 2420/07;
(Continued)

(56) References Cited

U.S. PATENT DOCUMENTS 10,827,249 B1 * 11/2020 Pine ...................... H04R 1/1041
10,860,114 B1 * 12/2020 Oommen ................ G06F 3/017
(Continued)

FOREIGN PATENT DOCUMENTS

JP            5185265 B2    4/2013
KR         10-1477285 B1    1/2015
KR      10-2016-0146307 A   12/2016

OTHER PUBLICATIONS

International Search Report dated Sep. 16, 2021, issued in International Application No. PCT/KR2021/006835.
(Continued)

*Primary Examiner* — Matthew A Eason
*Assistant Examiner* — Kuassi A Ganmavo
(74) *Attorney, Agent, or Firm* — Jefferson IP Law, LLP

(57) ABSTRACT

An audio output device is provided. The audio output device includes a buffering member including a biometric sensor and a first terminal connected to the biometric sensor, a housing including a portion to which the buffering member is mounted, a second terminal disposed in the portion of the housing and electrically connected to the first terminal of the buffering member, and a control circuit positioned inside the housing and operatively connected to the biometric sensor, the first terminal, and the second terminal, wherein the control circuit may be configured to supply power to the biometric sensor through the second terminal if the first terminal and the second terminal are connected, and to receive at least one piece of biometric signal data obtained from the biometric sensor of the buffering member through the second terminal.

12 Claims, 14 Drawing Sheets

(51) Int. Cl.
*A61B 5/00* (2006.01)
*A61B 5/11* (2006.01)
*A61B 5/024* (2006.01)
*A61B 5/0205* (2006.01)
*A61B 5/1455* (2006.01)

(52) U.S. Cl.
CPC .......... *A61B 5/0022* (2013.01); *A61B 5/0205* (2013.01); *A61B 5/02427* (2013.01); *A61B 5/11* (2013.01); *A61B 5/1118* (2013.01); *A61B 5/1123* (2013.01); *A61B 5/14551* (2013.01); *A61B 5/6803* (2013.01); *A61B 5/742* (2013.01); *H04R 1/1016* (2013.01); *H04R 2201/105* (2013.01); *H04R 2420/07* (2013.01)

(58) Field of Classification Search
CPC ................ G06F 21/32; A61B 5/14551; A61B 5/02427; A61B 5/0205; A61B 5/11; A61B 5/6803; A61B 5/742; A61B 5/0022; A61B 5/1123; A61B 2562/0219; A61B 5/1118
See application file for complete search history.

(56) References Cited

U.S. PATENT DOCUMENTS

| | | | |
|---|---|---|---|
| 2008/0013747 A1* | 1/2008 | Tran | A61B 5/0295 381/67 |
| 2010/0113948 A1* | 5/2010 | Yang | A61B 5/02416 600/500 |
| 2013/0131519 A1* | 5/2013 | LeBoeuf | A61B 5/1455 600/476 |
| 2016/0094899 A1* | 3/2016 | Aumer | A61B 5/6802 340/870.07 |
| 2016/0254850 A1 | 9/2016 | Chen et al. | |
| 2016/0287108 A1* | 10/2016 | Wei | A61B 5/02433 |
| 2017/0311069 A1* | 10/2017 | Prevoir | H04R 1/1058 |
| 2017/0359660 A1 | 12/2017 | Nikookhoy et al. | |
| 2018/0235540 A1* | 8/2018 | Kirszenblat | A61B 5/296 |
| 2018/0373212 A1* | 12/2018 | Lin | G05B 19/0423 |
| 2019/0029529 A1* | 1/2019 | Haartsen | A61B 5/02438 |
| 2019/0099130 A1* | 4/2019 | LeBoeuf | A61B 5/6817 |
| 2019/0208304 A1* | 7/2019 | Cohen | H04R 25/652 |
| 2019/0306613 A1 | 10/2019 | Qian et al. | |
| 2020/0304898 A1* | 9/2020 | Cohen | H04R 1/1016 |
| 2021/0084402 A1* | 3/2021 | Terlizzi | H04R 1/1041 |
| 2022/0087609 A1* | 3/2022 | Ayers | A61B 5/02405 |

OTHER PUBLICATIONS

Written Opinion dated Sep. 16, 2021, issued in International Application No. PCT/KR2021/006835.

* cited by examiner

AUDIO OUTPUT DEVICE FOR OBTAINING BIOMETRIC DATA AND METHOD OF OPERATING SAME

CROSS-REFERENCE TO RELATED APPLICATION(S)

This application is based on and claims priority under 35 U.S.C. § 119(a) of a Korean patent application number 10-2020-0068584, filed on Jun. 5, 2020, in the Korean Intellectual Property Office, the disclosure of which is incorporated by reference herein in its entirety.

BACKGROUND

1. Field

The disclosure relates to an audio output device including a buffering member. More particularly, the disclosure relates to a biometric sensor inside a buffering member of an audio output device, thereby obtaining more accurate biometric data.

2. Description of Related Art

Earphones may be classified into open-type earphones and canal-type earphones depending on the wearing method. The open-type earphone is worn in the concha of a user's ear, whereby the earphone unit is not inserted into the canal. When the user wears the open-type earphone, a gap may be formed between the user's eardrum and the earphone unit, so it may not be possible to block surrounding noise. In addition, in the case of the open-type earphone, the wearing comfort may differ depending on the shape of the user's ear.

The canal-type earphone may be configured such that the earphone unit thereof is inserted into the ear canal of the user. If the user wears the canal-type earphone, the ear canal of the user may be substantially sealed, thereby blocking surrounding noise. In addition, the canal-type earphone may include a separate ear tip, and the ear tip (or a foam tip) may be replaced depending on the size of the user's ear.

With the recent advent of Bluetooth earphones, earphones may be divided into open-type Bluetooth earphones and canal-type Bluetooth earphones. Bluetooth earphones allow the user to make calls and enjoy music by interlocking with electronic devices (e.g., smartphones, personal computers (PCs), and the like) through Bluetooth pairing. Thanks to the activity and convenience provided to the user, unlike existing wired earphones, the number of users who use Bluetooth earphones is increasing. In addition, Bluetooth earphones equipped with a biometric sensor make it easier to obtain biometric data from the user, and are thus being commercialized as a health care product.

The above information is presented as background information only to assist with an understanding of the disclosure. No determination has been made, and no assertion is made, as to whether any of the above might be applicable as prior art with regard to the disclosure.

SUMMARY

As a biometric sensor is added to a Bluetooth earphone, the size and weight of the earphone unit may be increased. The earphone unit having increased size and weight may deteriorate the wearing comfort when the user wears the same for a long time. In addition, since the Bluetooth earphone, which is a small electronic device, may have a limited internal structure, it may be difficult to place a biometric sensor at an appropriate position.

In the case where the biometric sensor is placed in the housing of the Bluetooth earphone, the biometric sensor may come into contact with the concha of the user's ear. However, since the shape of the concha differs between users, the biometric sensor may not come into appropriate contact with the concha of the user. As the biometric sensor moves away from the user's skin, noise due to an external light source and motion noise due to the user's motion may occur.

Aspects of the disclosure are to address at least the above-mentioned problems and/or disadvantages and to provide at least the advantages described below. Accordingly, an aspect of the disclosure is to provide a biometric sensor inside a buffering member of an audio output device, thereby obtaining more accurate biometric data.

The technical issues to be addressed in the disclosure are not limited to the technical problems mentioned above, and other technical problems that are not mentioned herein may be clearly understood by those of ordinary skill in the art to which the disclosure pertains from the following description.

Additional aspects will be set forth in part in the description which follows and, in part, will be apparent from the description, or may be learned by practice of the presented embodiments.

In accordance with an aspect of the disclosure, an audio output device is provided. The audio output device includes a buffering member including a biometric sensor and a first terminal connected to the biometric sensor, a housing including a portion to which the buffering member is mounted, a second terminal disposed in the portion of the housing and electrically connected to the first terminal of the buffering member, and a control circuit positioned inside the housing and operatively connected to the biometric sensor, the first terminal, and the second terminal, wherein the control circuit may be configured to supply power to the biometric sensor through the second terminal if the first terminal and the second terminal are connected, and to receive at least one piece of biometric signal data obtained from the biometric sensor of the buffering member through the second terminal.

In accordance with another aspect of the disclosure, a method of operating an audio output device is provided. The method includes if a first terminal disposed in a buffering member and connected to a biometric sensor and a second terminal disposed in a portion of a housing to which the buffering member is mounted are connected, supplying power to the biometric sensor through the second terminal, and receiving at least one piece of biometric signal data obtained from the biometric sensor of the buffering member through the second terminal.

An audio output device and a method according to various embodiments make it possible to obtain improved biometric data by providing a biometric sensor inside the device so as to come into contact with the ear canal of a user.

An audio output device and a method according to various embodiments make it possible to improve the wearing comfort by disposing a biometric sensor in the buffering member and reducing the overall size and weight of the audio output device.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1A:
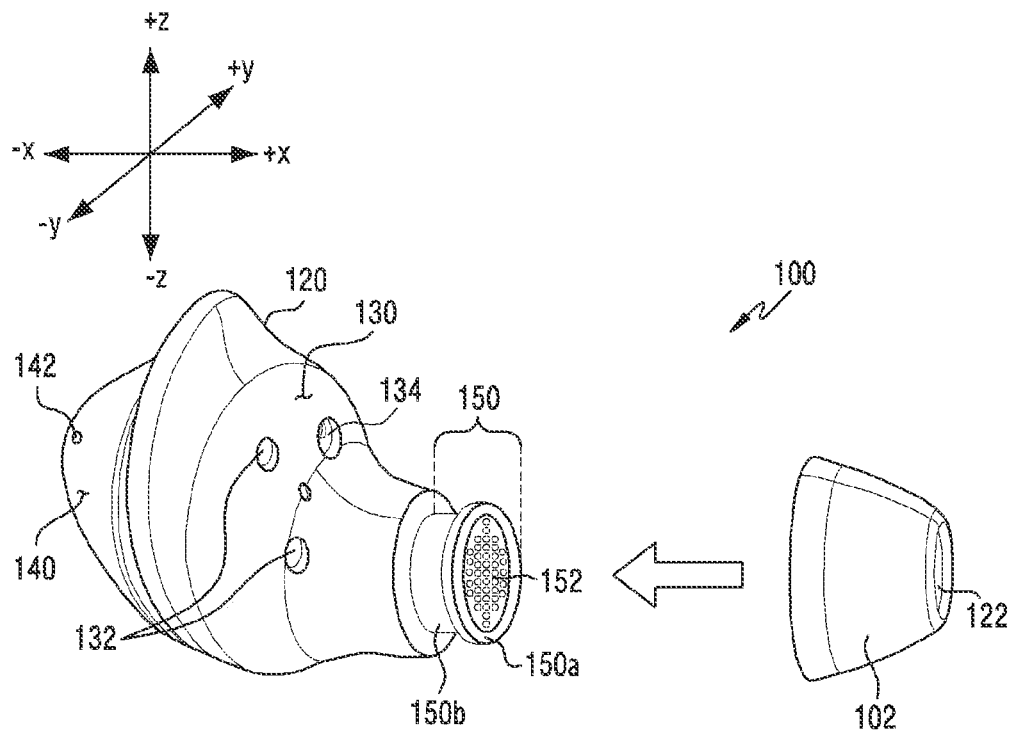
FIG. 1A is a perspective view illustrating an audio output device in a state before a housing and a buffering member are coupled to each other according to an embodiment of the disclosure.
Figure 1B:
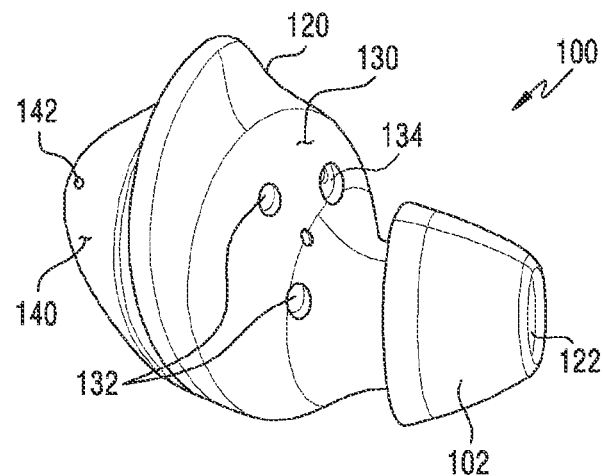
FIG. 1B is a perspective view illustrating an audio output device in a state after a housing and a buffering member are coupled to each other according to an embodiment of the disclosure.

FIG. 1A is a perspective view illustrating an audio output device in a state before a housing and a buffering member are coupled to each other according to an embodiment of the disclosure, and FIG. 1B is a perspective view illustrating an audio output device in a state after a housing and a buffering member are coupled to each other according to an embodiment of the disclosure.

Referring to FIGS. 1A and 1B, an audio output device 100 may include a housing 120 and a buffering member 102. FIG. 1A illustrates the state before the housing 120 and the buffering member 102 are coupled to each other, and FIG. 1B illustrates the state after the housing 120 and the buffering member 102 are coupled to each other.

In an embodiment of the disclosure, the housing 120 of the audio output device 100 may have a first outer surface 130 and a second outer surface 140. The first outer surface 130 may indicate the region of the housing 120 that comes into contact with the user's ear and is disposed to face the +x direction. The second outer surface 140 may indicate the region of the housing 120 that does not come into contact with the user's ear and is disposed to face the −x direction. In an embodiment of the disclosure, a charging interface 132 and a wear detection sensor 134 may be disposed in portions of the first outer surface 130. In an embodiment of the disclosure, the audio output device 100 may receive power from a separate external power supply (e.g., a charging case) through the charging interface 132. In an embodiment of the disclosure, the wear detection sensor 134 may include at least one of a proximity sensor, a touch (grip) sensor, an atmospheric pressure sensor, a sound wave sensor, or a motion sensor. In an embodiment of the disclosure, the audio output device 100 may detect whether or not the audio output device 100 is worn on an external object (e.g., a user) through the wear detection sensor 134.

In an embodiment of the disclosure, the proximity sensor may detect whether or not the audio output device 100 is worn on an external object (e.g., a user) using an optical method, a radio frequency (RF) method, or a sound wave method. For example, a plurality of proximity sensors using an optical method may be disposed depending on the positions where they are disposed.

In an embodiment of the disclosure, the touch (grip) sensor may detect whether or not the audio output device 100 is worn on an external object (e.g., a user's skin) using a capacitive method. In an embodiment of the disclosure, in order to detect whether or not the audio output device 100 is worn on an external object (e.g., a user), the touch (grip)

sensor may be disposed in at least a portion of the housing 120 depending on the curved shape of the housing 120 of the audio output device 100.

In an embodiment of the disclosure, the atmospheric pressure sensor may detect whether or not the audio output device 100 is worn on an external object (e.g., a user) using a difference in atmospheric pressure that occurs when the audio output device 100 is worn on the external object (e.g., the user).

In an embodiment of the disclosure, the sound wave sensor may include a plurality of microphones, and may detect whether or not the audio output device 100 is worn on an external object (e.g., a user) by analyzing patterns of sound waves collected through the plurality of microphones. For example, it is possible to detect whether or not the audio output device 100 is worn on an external object (e.g., a user) by outputting an audio signal of a specified frequency using a speaker and comparing the difference between the audio signals received by at least two microphones.

In an embodiment of the disclosure, the motion sensor may detect whether or not the audio output device 100 is worn on an external object (e.g., a user) by identifying the wearing motion of the external object (e.g., the user).

In an embodiment of the disclosure, the housing 120 may include a protrusion 150 protruding from a portion of the first outer surface 130 in a first direction (the x direction). The protrusion 150 is a portion to be inserted into the ear canal of the user, and may be formed in a cylindrical shape. In an embodiment of the disclosure, the shape of the protrusion 150 is not limited thereto, and may be variously modified depending on the design of a manufacturer. In an embodiment of the disclosure, at least a portion of the protrusion 150 may include a vertical step. For example, since the protrusion 150 includes a vertical step, the diameter of one region 150a of the protrusion 150 may be greater than the diameter of another region 150b. In an embodiment of the disclosure, referring to the state shown in FIG. 1B, as one region 150a of the protrusion 150, which has a large diameter, is inserted into one region of the buffering member 102, at least a portion of the housing 120 may be coupled to the buffering member 102.

In an embodiment of the disclosure, the protrusion 150 may include a speaker 152 in a portion thereof. The speaker 152 may include a voice coil, a diaphragm, and a magnet. In addition, the speaker 152 may include a structure (e.g., a wire mesh) to prevent the inflow of foreign matter from the outside. In an embodiment of the disclosure, the structure may be disposed on the outer surface of one region of the protrusion 150, and the components of the speaker (e.g., the voice coil, the diaphragm, and the magnet) may be disposed inside the protrusion 150.

In an embodiment of the disclosure, the buffering member 102 may have a through-hole 122. For example, when the buffering member 102 is coupled to the housing 120, the voice (audio) output from the speaker 152 may be transferred to an external object (e.g., a user) through the through-hole 122 in the buffering member 102. In an embodiment of the disclosure, the buffering member 102 may be formed of a silicon material. For example, at least a portion of the buffering member 102 may be deformed according to the shape of the external object (e.g., the shape of the ear canal). In an embodiment of the disclosure, the buffering member 102 may be formed of a combination of at least two of silicon, foam, and plastic materials. For example, a region of the buffering member 102 that is inserted into and comes into contact with the user's ear may be formed of a silicon material, and a region into which the housing 120 is inserted may be formed of a plastic material.

In an embodiment of the disclosure, a touch pad (not shown) and at least one microphone 142 may be disposed on the second outer surface 140 of the housing 120. In an embodiment of the disclosure, the touch pad may receive a touch input from the user. For example, the audio output device 100 may perform operations of receiving and terminating calls, reproducing content, and pausing the same through a touch input of the user onto the touch pad. In an embodiment of the disclosure, in the case where two microphones 142 are disposed on the second outer surface 140, the two microphones may be disposed to be spaced apart from each other.

Figure 2:
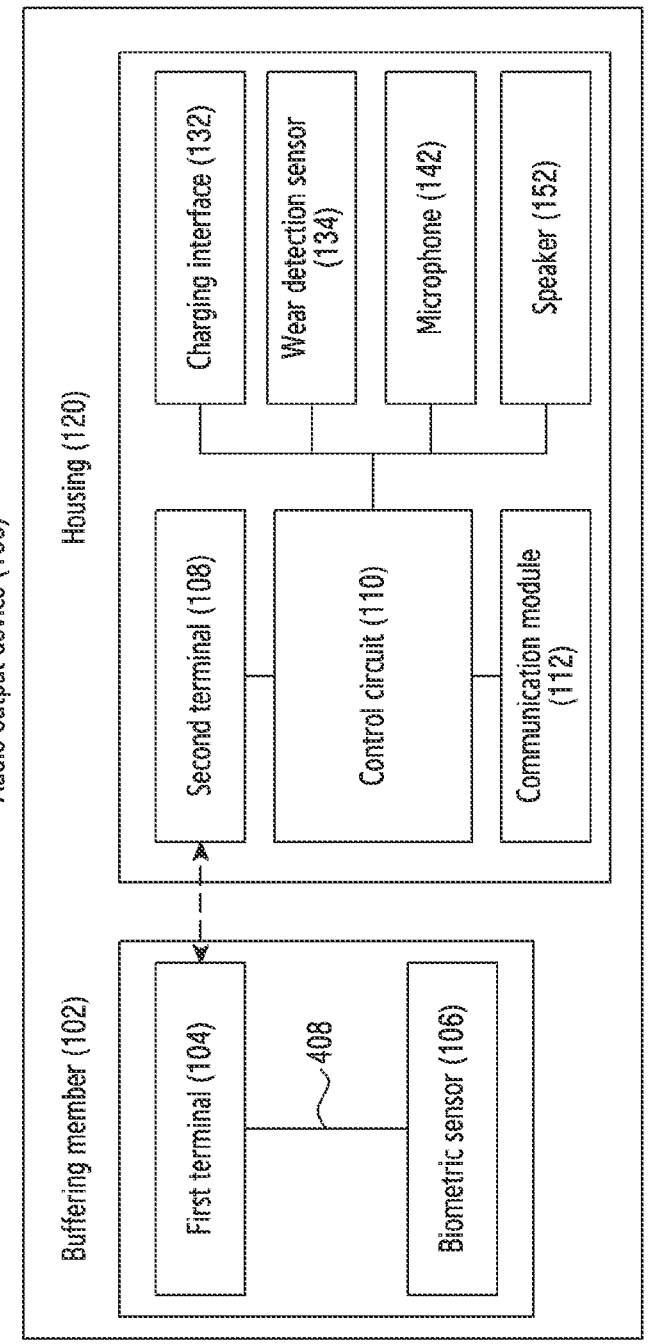
FIG. 2 is a block diagram of an audio output device according to an embodiment of the disclosure.

FIG. 2 is a block diagram of an audio output device according to an embodiment of the disclosure.

Referring to FIG. 2, the audio output device 100 may include a buffering member 102 and a housing 120. In this document, the term "module" may be understood as hardware or a circuit for performing a predetermined function.

In an embodiment of the disclosure, the buffering member 102 may include a first terminal 104 and a biometric sensor 106.

In an embodiment of the disclosure, the biometric sensor 106 may detect a user's state, and may obtain biometric signal data corresponding to the detected state. In an embodiment of the disclosure, the biometric sensor 106 may include at least one of a heart-rate monitor (HRM) sensor and a saturation-of-percutaneous oxygen ($SpO_2$) sensor. In an embodiment of the disclosure, the biometric sensor 106 may include at least one light emitter {e.g., a light-emitting diode (LED)} and at least one light receiver {e.g., a photodiode (PD)}. However, the at least one light emitter is not limited to the light-emitting diode (LED), and may include at least one of an organic light-emitting diode (OLED), a laser diode (LD), a solid laser, or an infrared (IR) diode. In addition, the at least one light receiver is not limited to the photodiode (PD), and may include at least one of an avalanche photo diode (APD), a phototransistor, or an image sensor. In an embodiment of the disclosure, the light emitter may emit a signal (e.g., green light, red light, infrared light, or the like) to the external object, and the light receiver may receive a reflected signal from the external object.

In an embodiment of the disclosure, the biometric sensor 106 may transmit biometric signal data to a control circuit 110 through the first terminal 104. For example, the light receiver of the biometric sensor 106 may convert biometric signal data in the form of an optical signal into an electrical signal. In the case where the first terminal 104 and the second terminal 108 are connected, the biometric sensor 106 may transmit the biometric signal data in the form of the converted electrical signal to the control circuit 110 through the first terminal 104 and the second terminal 108.

In an embodiment of the disclosure, the housing 120 may include a control circuit 110, a second terminal 108, a communication module 112, a charging interface 132, a wear detection sensor 134, a microphone 142, or a speaker 152. The charging interface 132, the wear detection sensor 134, the microphone 142, or the speaker 152 according to an embodiment of the disclosure have been described above with reference to FIGS. 1A and 1B.

In an embodiment of the disclosure, the control circuit 110 may detect whether or not the buffering member 102 is mounted through the second terminal 108. For example, the control circuit 110 may detect a change in the resistance value of the second terminal 108, thereby detecting whether or not the buffering member 102 is mounted. In an embodiment of the disclosure, the control circuit 110 may supply current to the biometric sensor 106 (e.g., at least one light emitter) of the buffering member 102 through the second terminal 108.

In an embodiment of the disclosure, the control circuit 110 may obtain biometric data, based on the biometric signal data received from the biometric sensor 106. For example, because the control circuit 110 receives the biometric signal data obtained in a time series from the biometric sensor 106, it is possible to obtain biometric data on at least one of a heart rate, oxygen saturation ($SpO_2$), heart rate variability (HRV), blood pressure, stress, blood sugar, and blood vessel status. For example, when the light emitter of the biometric sensor 106 emits an optical signal having a first amount of light to the user's skin, the light receiver may receive an optical signal reflected by blood vessels in the skin. In this case, the reflected light signal may have a second amount of light, which is less than the first amount of light. The control circuit 110 may receive biometric signal data having the second amount of light from the light receiver of the biometric sensor 106. The control circuit 110 may calculate a change in the amount of light (e.g., a value corresponding to "first amount of light−second amount of light"), based on the biometric signal data, and may obtain biometric data, based on the change in the amount of light. In an embodiment of the disclosure, the biometric sensor 106 may transmit the obtained biometric data to the first terminal 104, which is connected via a connection member 408.

In an embodiment of the disclosure, the audio output device 100 may transmit at least one piece of biometric data to an external electronic device through the communication module 112. For example, when the audio output device 100 is connected to an external electronic device through short-range communication (e.g., Bluetooth) using the communication module 112, the audio output device 100 may transmit data on a heart rate (e.g., about 65 bpm) to the external electronic device.

Although FIG. 2 illustrates the buffering member 102 including the biometric sensor 106, the disclosure is not limited thereto. In an embodiment of the disclosure, the buffering member 102 may include at least one of a gyro sensor, an acceleration sensor, a proximity sensor, a temperature sensor, a humidity sensor, and an illuminance sensor. Further, the first terminal 104 and the second terminal 108 in FIG. 2 will be described in detail later with reference to FIGS. 3 to 10.

Figure 3:
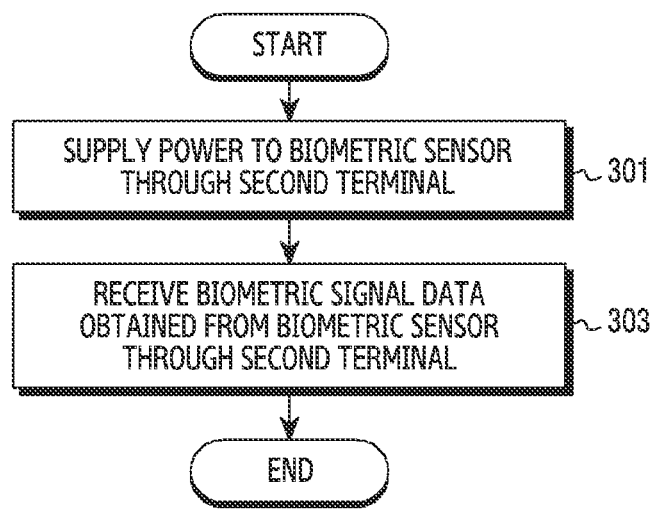
FIG. 3 is a flowchart illustrating an operation of an audio output device according to an embodiment of the disclosure.

FIG. 3 is a flowchart illustrating an operation of an audio output device according to an embodiment of the disclosure. A description that corresponds to the description made in connection with the above embodiments or is the same or similar thereto may be omitted from the description of FIG. 3.

Referring to FIG. 3, an audio output device (e.g., the audio output device 100 in FIGS. 1A, 1B, and 2 or the control circuit 110 in FIG. 2) may supply power to a biometric sensor (e.g., the biometric sensor 106 in FIG. 2) through a second terminal (e.g., the second terminal 108 in FIG. 2) in operation 301. In an embodiment of the disclosure, the audio output device 100 may supply current to the biometric sensor 106 after detecting that a buffering member (e.g., the buffering member 102 in FIG. 2) is mounted through the second terminal 108. For example, the audio output device 100 may detect a change in the resistance value of the second terminal 108 according to the connection between a first terminal (e.g., the first terminal 104 in FIG. 2) and the second terminal 108. At the time at which a change in the resistance value is detected in the second terminal 108, the audio output device 100 may start charging the biometric sensor 106 through the second terminal 108.

According to an embodiment of the disclosure, the audio output device 100 may receive biometric signal data obtained from the biometric sensor 106 through the second terminal 108 in operation 303. For example, the audio output device 100 may receive biometric signal data through power line communication (PLC) according to the connection between the first terminal 104 and the second terminal 108.

In an embodiment of the disclosure, the audio output device 100 may receive biometric signal data only when proximity of an external object (e.g., a user) is detected. For example, a control circuit (e.g., the control circuit 110 in FIG. 2) may perform control to detect wearing by the user through a proximity sensor (e.g., the wear detection sensor 134 in FIGS. 1A and 1B) and to emit a signal (e.g., LED light) through the biometric sensor (e.g., the biometric sensor 106 in FIG. 2) only when the wearing is detected. In an embodiment of the disclosure, the audio output device 100 may receive biometric signal data through connection with an external electronic device. For example, the control circuit 110 may establish short-range communication {e.g., Bluetooth or Bluetooth low energy (BLE)} with an external electronic device (e.g., a smart phone) through a communication module (e.g., the communication module 112 in FIG. 2). When the short-range communication is established, the control circuit 110 may perform control to emit a signal through the biometric sensor 106. In another example, when a specific application (e.g., a "Samsung health" application) is executed in an external electronic device connected through short-range communication, the control circuit 110 may perform control to emit a signal through the biometric sensor 106.

In an embodiment of the disclosure, a method of operating an audio output device to be worn in the ear of a user may include if a first terminal disposed in a buffering member and connected to a biometric sensor and a second terminal disposed in a portion of a housing to which the buffering member is mounted are connected, supplying power to the biometric sensor through the second terminal, and receiving at least one piece of biometric signal data obtained from the biometric sensor of the buffering member through the second terminal.

In an embodiment of the disclosure, the buffering member may include a connection portion formed to be connected to the portion of the housing, and a cover formed to extend from the connection portion so as to surround the connection portion, and one region of the portion of the housing may be formed to protrude, and may be inserted into the connection portion of the buffering member.

In an embodiment of the disclosure, the first terminal may be disposed in a portion of the connection portion of the buffering member, and the biometric sensor may be disposed inside the cover of the buffering member.

In an embodiment of the disclosure, the first terminal and the biometric sensor of the buffering member may be connected through at least one of a flexible printed circuit board (FPCB) and a wire.

In an embodiment of the disclosure, the one region of the portion of the housing may include an embossed protrusion, and a portion of the connection portion of the buffering member may include a recessed groove formed to correspond to the embossed protrusion, wherein the housing and the buffering member may be coupled in one direction.

In an embodiment of the disclosure, the first terminal may include a 1-$1^{st}$ terminal and a 1-$2^{nd}$ terminal, and the second terminal may include a 2-$1^{st}$ terminal corresponding to the 1-1$^{st}$ terminal and a 2-2$^{nd}$ terminal corresponding to the 1-2$^{nd}$ terminal, wherein if the housing and the buffering member are coupled in the one direction, the 1-1$^{st}$ terminal and the 2-1$^{st}$ terminal may come into contact with each other, and the 1-2$^{nd}$ terminal and the 2-2$^{nd}$ terminal may come into contact with each other.

In an embodiment of the disclosure, the operation method may further include receiving first biometric signal data obtained from a first biometric sensor including a first light emitter and a first light receiver disposed adjacent to the first light emitter, receiving second biometric signal data obtained from a second biometric sensor including a second light emitter and a second light receiver disposed adjacent to the second light emitter, comparing signal quality information of the first biometric signal data with signal quality information of the second biometric signal data, and if the signal quality information of the first biometric signal data has a higher signal quality value than that of the second biometric signal data, selecting the first biometric signal data.

In an embodiment of the disclosure, the operation method may further include comparing the signal quality information, based on a signal-to-noise ratio (SNR) value of the first biometric signal data and an SNR value of the second biometric signal data.

In an embodiment of the disclosure, the buffering member may be formed by silicon molding on at least a portion of the biometric sensor.

In an embodiment of the disclosure, the operation method may further include transmitting at least one piece of the obtained biometric signal data to an external electronic device through a communication module.

Figure 4A:
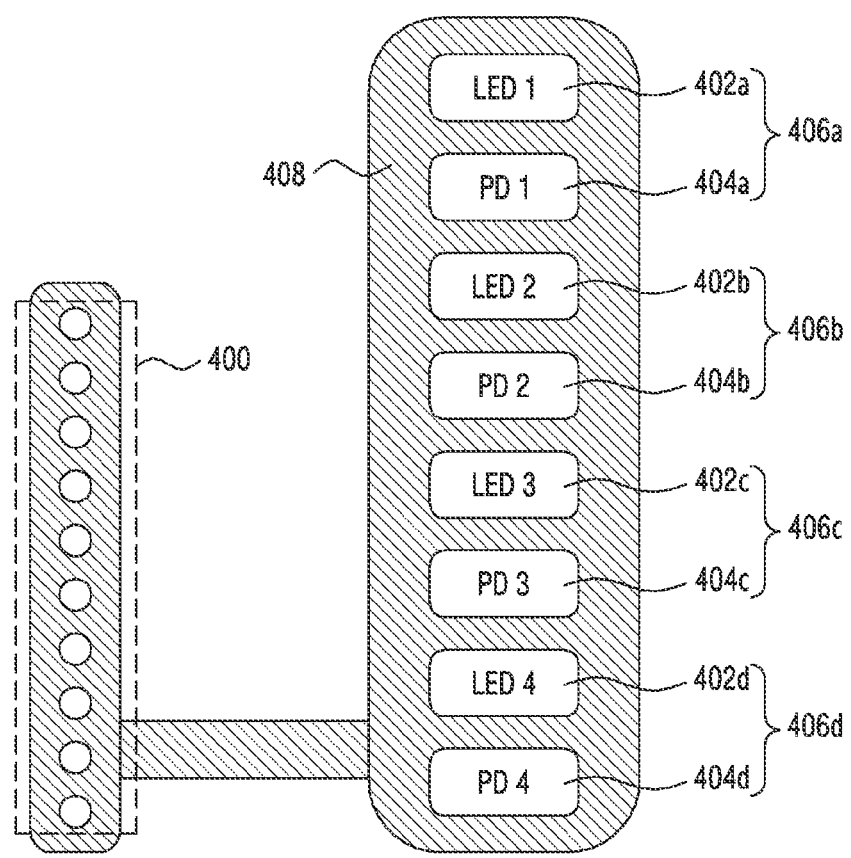
FIG. 4A illustrates a structure of a connection member in which a first terminal and a biometric sensor are disposed according to an embodiment of the disclosure.

FIG. 4A illustrates a structure of a connection member in which first terminals and biometric sensors are disposed according to an embodiment of the disclosure.

Referring to FIG. 4A, first terminals 400 (e.g., the first terminal 104 in FIG. 2) and biometric sensors 406 (e.g., the biometric sensor 106 in FIG. 2) may be arranged to be spaced apart from each other on a connection member 408. In an embodiment of the disclosure, the first terminals 400 may include one or more terminals. In an embodiment of the disclosure, at least a portion of the connection member 408 may be formed of a bendable material. For example, the connection member 408 may correspond to at least one of a printed circuit board {e.g., a flexible printed circuit board (FPCB) or a rigid-flexible PCB (RFPCB)) formed of a polyimide material and a metal wire.

In an embodiment of the disclosure, the biometric sensors 406 may include one or more light emitters 402a, 402b, 402c, and 402d and one or more light receivers 404a, 404b, 404c, and 404d. For example, the biometric sensors 406 may include a first biometric sensor 406a including one light emitter 402a (e.g., LED 1) and one light receiver 404a (e.g., PD 1). The biometric sensors 406 may be configured such that a plurality of biometric sensors (e.g., a first biometric sensor 406a, a second biometric sensor 406b, a third biometric sensor 406c, and a fourth biometric sensor 406d) is arranged in an array form. As another example, the biometric sensors 406 may include a plurality of light emitters {e.g., LED 1 (402a), LED 2 (402b), LED 3 (402c), and LED 4 (402d)} and a plurality of light receivers {e.g., PD 1 (404a), PD 2 (404b), PD 3 (404c), and PD 4 (404d)}.

In an embodiment of the disclosure, the number of first terminals 400 may be determined according to the number of light emitters 402 and light receivers 404 of the biometric sensors 406. For example, two first terminals 400 may be disposed in each of one light emitter 402 and one light receiver 404. The first terminals 400 may include one power terminal and one LED driver terminal, which are disposed in one light emitter 402. In addition, the first terminals 400 may include one ground terminal and one PD terminal, which are disposed in one light receiver 404. In an embodiment of the disclosure, in the case where the biometric sensors 406 include one light emitter 402 and one light receiver 404, four first terminals 400 may be disposed in the connection member 408. In an embodiment of the disclosure, the number of first terminals 400 may be determined according to the number of channels to be driven. For example, in the case where the biometric sensors 406 include four light emitters 402 and four light receivers 404 and where four light receivers 404 are connected to one analog-to-digital converter (ADC), the biometric sensors 406 may be driven through one channel. The biometric sensors 406 driven through one channel may summate signal values received from the respective light receivers 404, and may output a single value, so the biometric sensors 406 may be implemented through a simple circuit. In this case, two first terminals 400 may be disposed with respect to the light emitters and the light receivers. As another example, in the case where the biometric sensors 406 include four light emitters 402 and four light receivers 404 and where four light receivers 404 are respectively connected to four ADCs, the biometric sensors 406 may be driven through four channels. The biometric sensors 406 driven through four channels may output a plurality of values, based on the signal values received from the respective light receivers 404, and may be implemented through a complex circuit. In this case, eight first terminals 400 may be disposed with respect to the light emitters and the light receivers. In an embodiment of the disclosure, the method of determining the number of first terminals 400 is not limited and may be determined to be different depending on the design of a manufacturer.

Figure 4B:
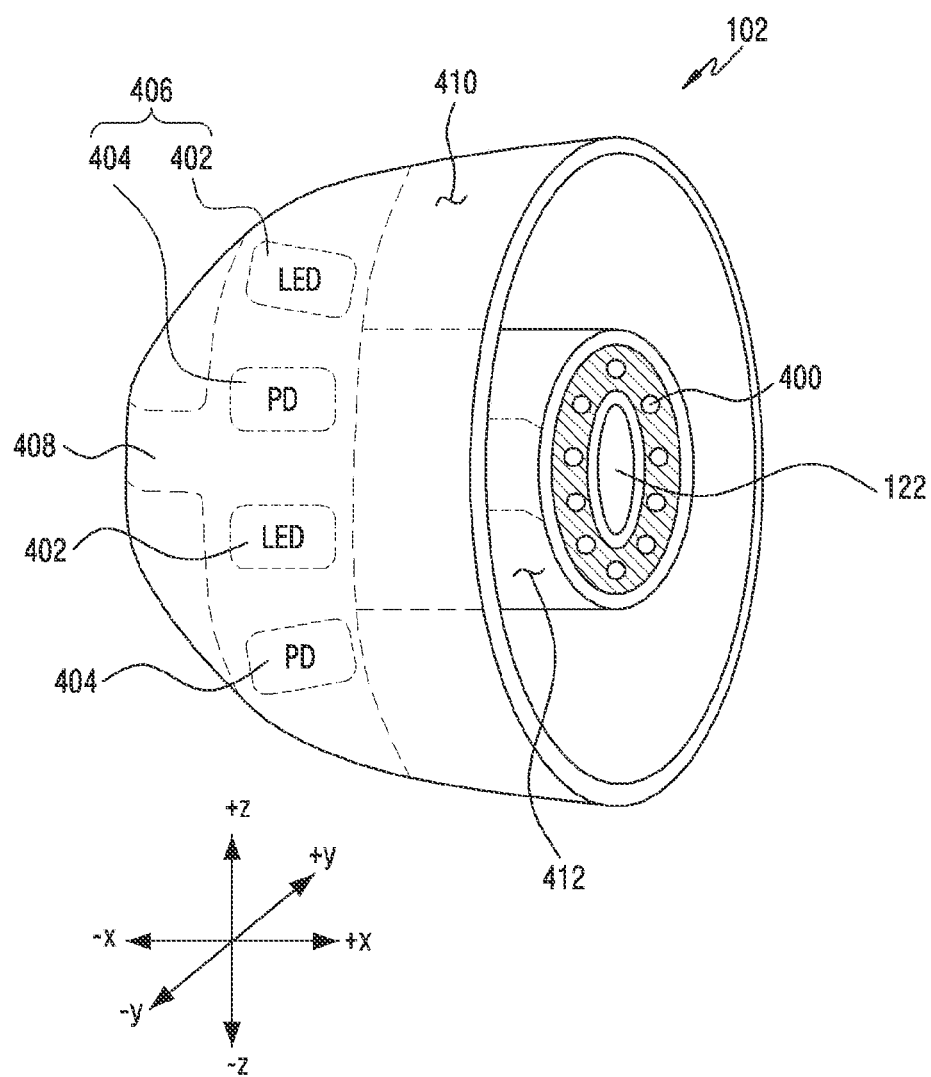
FIG. 4B illustrates a structure of a buffering member to which a first terminal and a biometric sensor are mounted according to an embodiment of the disclosure.

FIG. 4B illustrates a structure of a buffering member to which a first terminal and a biometric sensor are mounted according to an embodiment of the disclosure.

Referring to FIG. 4B, a buffering member 102 may include a connection portion 412 to be coupled to a portion of a housing (e.g., the housing 120 in FIGS. 1A and 1B) and a cover 410 formed to surround the connection portion 412. In an embodiment of the disclosure, the buffering member 102 may be formed by silicon molding for the connection member 408 in FIG. 4A.

In an embodiment of the disclosure, the connection portion 412 of the buffering member 102 may include a through-hole 122 into which a portion of the housing 120 is inserted. For example, when the buffering member 102 is mounted to the housing 120, a protrusion of the housing 120 (e.g., the protrusion 150 in FIG. 1A) may be inserted into the through-hole 122 of the connection portion 412. In an embodiment of the disclosure, at least a portion of the connection portion 412 may be formed to correspond to the housing 120. For example, in the case where the outer surface of the protrusion 150 of the housing 120 includes a curved surface, the inner side of the connection portion 412 may be formed to correspond to the curved surface of the protrusion 150. As another example, in the case where the protrusion 150 of the housing 120 includes a vertical step, the inner side of the connection portion 412 may be formed to correspond to the vertical step.

In an embodiment of the disclosure, the connection portion 412 may include a first surface facing a first direction, a second surface forming an outer surface of a sidewall formed to surround the first surface, and a third surface forming the inner side of the sidewall.

In an embodiment of the disclosure, first terminals 400 may be disposed on the first surface of the connection portion 412 so as to come into contact with second terminals (e.g., the second terminal 108 in FIG. 2) of the housing 120. For example, a first portion of the connection member 408 in which the first terminals 400 are disposed may be formed in a rectangular shape as shown in FIG. 4A. In the case where the first portion is disposed on the first surface, the first portion may be bent such that the first terminal 400 faces the first direction. As another example, the first portion of the connection member 408 including the first terminals 400 may be formed in an annular band shape (e.g., a donut shape) so as to correspond to the shape of the first surface. In an embodiment of the disclosure, the first terminals 400 disposed in the connection member 408 may be formed to be exposed to the outside without being molded using silicon.

In an embodiment of the disclosure, at least a portion of the connection portion 412 may extend, thereby forming the cover 410. For example, the second surface forming the outer surface of the sidewall of the connection portion 412 may extend in the −x direction, and may then be curved in the +x direction and extend, thereby forming the inner side of the cover 410. The third surface forming the inner side of the sidewall of the connection portion 412 may extend in the −x direction, and may then be curved in the +x direction to extend, thereby forming the outer surface of the cover 410. In an embodiment of the disclosure, at least a portion of the cover 410 may come into contact with an external object (e.g., a user), and the cover 410 may be formed to have a curved surface. In an embodiment of the disclosure, the cover 410 may be formed of a silicon material or a foam material so as to be deformed to correspond to the external object. For example, as the cover 410 is inserted into the user's ear, the cover 410 may be deformed to correspond to the inner shape of the user's ear.

In an embodiment of the disclosure, the biometric sensor 406 may be disposed on the side surface (e.g., the outer surface) of the cover 410. For example, a second portion of the connection member 408 in which the biometric sensor 406 is disposed may be formed in a rectangular shape as shown in FIG. 4A. The second portion may be bent so as to correspond to the shape (e.g., a curved surface) of the side surface of the cover 410.

In an embodiment of the disclosure, the connection member 408 may be mounted inside the buffering member 102 so as not to be exposed to the outside. In an embodiment of the disclosure, a silicon layer may be formed on one side of the connection member 408 (e.g., the front surface on which the first terminal and the biometric sensor are disposed) by silicon molding, and the opposite side of the connection member 408 (e.g., a rear surface thereof) may be exposed to the outside.

In an embodiment of the disclosure, the connection member 408 may connect the first portion in which the first terminals 400 are disposed with the second portion in which the biometric sensors 406 are disposed. For example, the connection member 408 mounted to the buffering member 102 may extend from the connection portion 412 of the buffering member 102 to the cover 410, thereby connecting the first portion and the second portion. As another example, the connection member 408 may extend through an opening provided in at least a portion of the buffering member 102, and may connect the first portion and the second portion.

Figure 5:
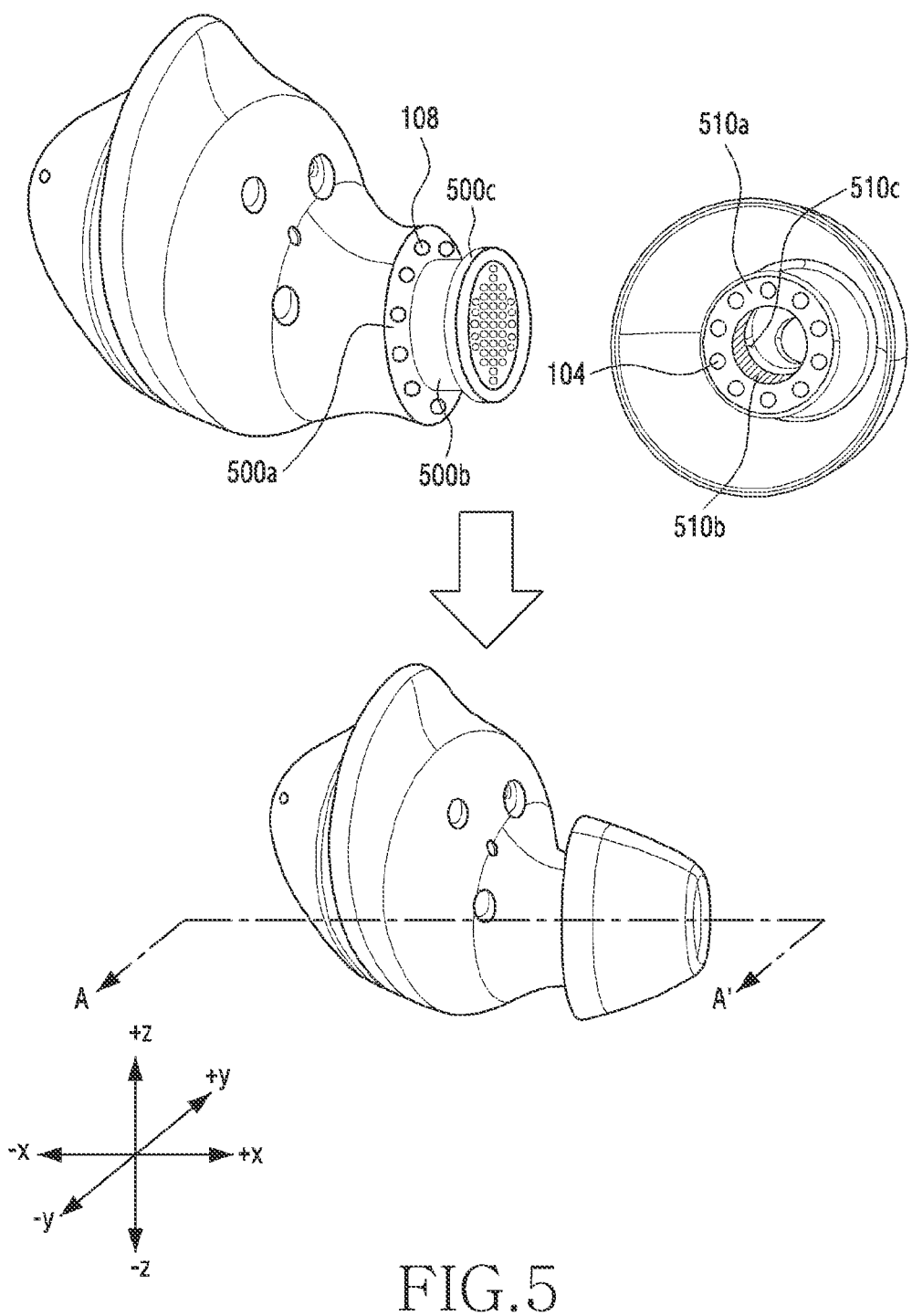
FIG. 5 illustrates a structure of a housing and a buffering member of an audio output device according to an embodiment of the disclosure.
Figure 6A:
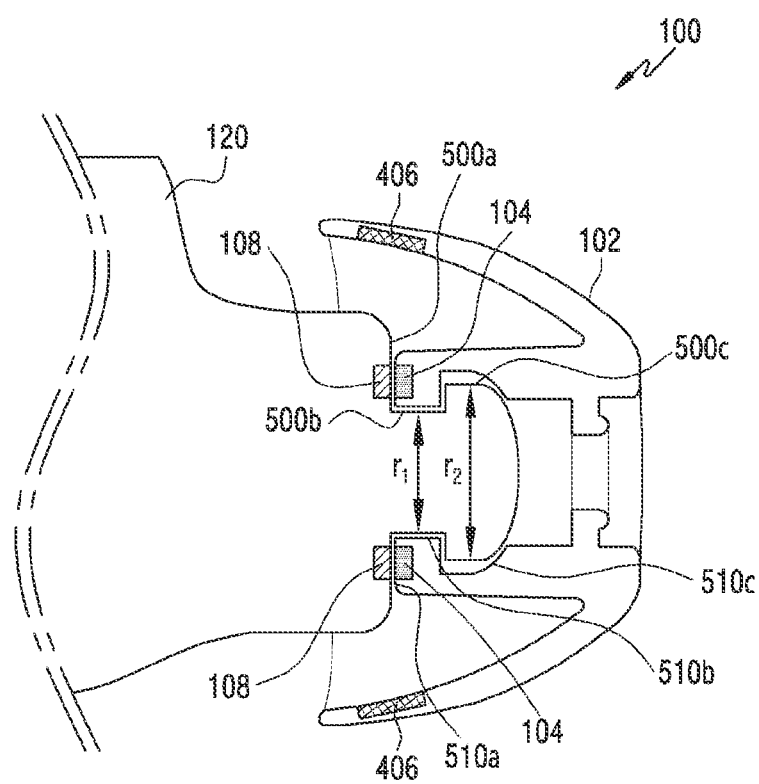
FIG. 6A is a cross-sectional view of an audio output device coupled in a first manner according to an embodiment of the disclosure.
Figure 6B:
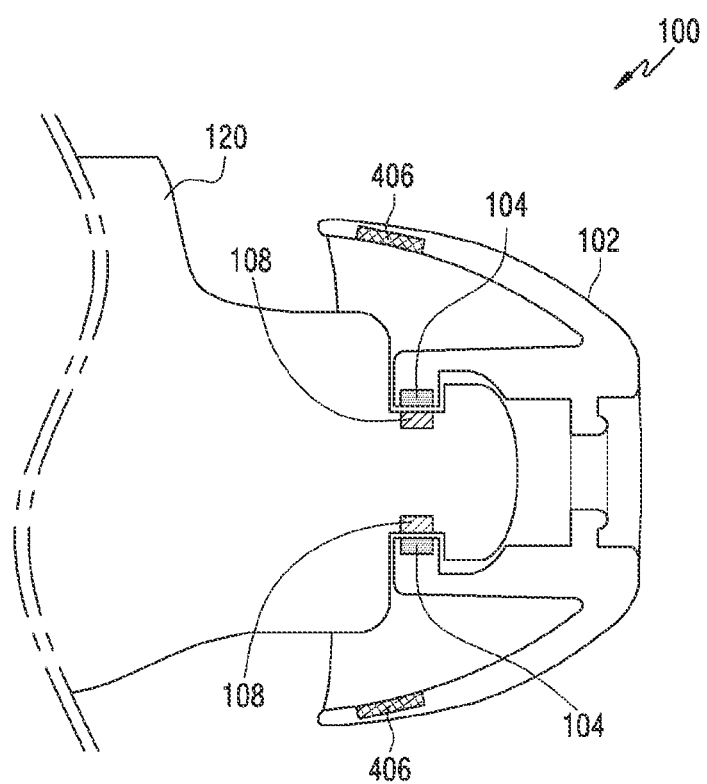
FIG. 6B is a cross-sectional view of an audio output device coupled in a second manner according to an embodiment of the disclosure.

FIG. 5 illustrates a structure of a housing and a buffering member of an audio output device according to an embodiment of the disclosure. FIG. 6A is a cross-sectional view of the audio output device in FIG. 5, which is coupled in a first manner, taken along the line A-A' and viewed in the −y-axis direction according to an embodiment of the disclosure. FIG. 6B is a cross-sectional view of the audio output device in FIG. 5, which is coupled in a second manner, taken along the line A-A' and viewed in the −y-axis direction according to an embodiment of the disclosure.

The housing and the buffering member are illustrated in FIGS. 6A and 6B such that they do not come into contact with each other for convenience of description. Therefore, in the case where the housing and the buffering member are coupled to each other, the outer surface of the housing and the inner side of the buffering member may come into contact with each other.

Referring to FIGS. 5, 6A, and 6B, second terminals 108 may be disposed in a portion of a housing 120 of the audio output device 100. In an embodiment of the disclosure, first terminals 104 may be disposed in a portion of the buffering member 102. The first terminals 104 and the second terminals 108 may include at least one of a power terminal, a ground (GND) terminal, an LED driver terminal, and a PD terminal, respectively. In an embodiment of the disclosure, if the buffering member 102 is mounted to the housing 120, the portion of the housing 120 may come into contact with a portion of the buffering member 102. In this case, at least one terminal (e.g., a power terminal) among the second terminals 108 disposed in the portion of the housing 120 may be connected to at least one terminal (e.g., a power terminal) among the first terminals 104 disposed in the portion of the buffering member 102.

In an embodiment of the disclosure, the housing 120 may include a protrusion (e.g., the protrusion 150 in FIG. 1A) protruding from a portion thereof, and the protrusion 150 may include a first surface 500a, a second surface 500b, and a third surface 500c. In an embodiment of the disclosure, the buffering member 102 may include a connection portion (e.g., the connection portion 412 in FIG. 4B), and the connection portion 412 may include a first surface 510a, a second surface 510b, and a third surface 510c.

In an embodiment of the disclosure, at least one second terminal 108 may be disposed on the first surface 500a of the housing 120 as shown in FIG. 6A. In this case, at least one first terminal 104 may be disposed on the first surface 510a of the buffering member 102. In an embodiment of the disclosure, at least one second terminal 108 may be disposed on the second surface 500b of the housing 120 as shown in FIG. 6B. In this case, at least one first terminal 104 may be disposed on the second surface 510b of the buffering member 102. In an embodiment of the disclosure, the protrusion (e.g., the protrusion 150 in FIG. 1A) of the housing 120 may be inserted into the connection portion (e.g., the connection portion 412 in FIG. 4B) of the buffering member 102. As the protrusion 150 is inserted into the connection portion 412, the first surface 500a of the housing 120 may come into contact with the first surface 510a of the buffering member 102, the second surface 500b of the housing 120 may come into contact with the second surface 510b of the buffering member 102, and the third surface 500c of the housing 120 may come into contact with the third surface 510c of the buffering member 102.

In an embodiment of the disclosure, the inner side (e.g., the through-hole 122 in FIGS. 1A and 1B) of the connection portion 412 of the buffering member 102 may be formed to correspond to the outer surface of the protrusion 150 of the housing 120. For example, in the case where the protrusion 150 includes a vertical step, the diameter of one region of the protrusion 150 may be $r_1$, and the diameter of the other region may be $r_2$, which is greater than $r_1$. The one region may indicate the region including the outer surface of the second surface 500b, and the other region may indicate the region including the outer surface of the third surface 500c. The diameter of one region of the connection portion 412, which corresponds to the one region of the protrusion 150, may be $r_1$, and the diameter of the other region of the connection portion 412, which corresponds to the other region of the protrusion 150, may be $r_2$. In an embodiment of the disclosure, the connection portion 412 having different diameters $r_1$ and $r_2$ may play the role of maintaining the buffering member 102 so as to prevent easy separation thereof from the housing 120.

In an embodiment of the disclosure, the buffering member 102 may be formed of a material (e.g., silicone, foam, or the like) capable of returning to the original state even if deformed by external force. For example, the diameter of one region (e.g., the entrance region) of the connection portion 412 of the buffering member 102 formed of a silicon material may be $r_1$, and the diameter of the other region (e.g., a speaker region) of the protrusion 150 may be $r_2$. The diameter of the one region of the connection portion 412 formed of a silicon material may increase (e.g., from $r_1$ to $r_2$) due to insertion of the protrusion 150, and may then return to the original value $r_1$.

In an embodiment of the disclosure, in the case where the first terminal 104 and the second terminal 108 are connected while in contact with each other as shown in FIGS. 6A and 6B, a control circuit (e.g., the control circuit 110 in FIG. 2) of the audio output device 100 may supply current to the biometric sensor 406. In an embodiment of the disclosure, as the current is received through the control circuit 110, the biometric sensor 406 may output a signal to the outside, and may receive a reflected signal.

Although FIGS. 6A and 6B illustrate only the audio output device in which the first terminals 104 are disposed on the first surface 510a or the second surface 510b of the buffering member 102 and in which the second terminals 108 are disposed on the first surface 500a or the second surface 500b of the housing 120, the disclosure is not limited thereto. In an embodiment of the disclosure, the first terminals 104 and the second terminals 108 may be disposed in regions that come into contact when the buffering member 102 and the housing 120 are connected (e.g., the third surface 510c of the buffering member and the third surface 500c of the housing). In an embodiment of the disclosure, the first terminals 104 may be disposed in at least two or more regions of the first surface 510a, the second surface 510b, and the third surface 510c of the buffering member, which are the regions that come into contact when the buffering member 102 and the housing 120 are connected, and the second terminals 108 may be disposed in at least two or more regions of the first surface 500a, the second surface 500b, and the third surface 500c of the housing 120, which are the regions that come into contact when the buffering member 102 and the housing 120 are connected.

Figure 7:
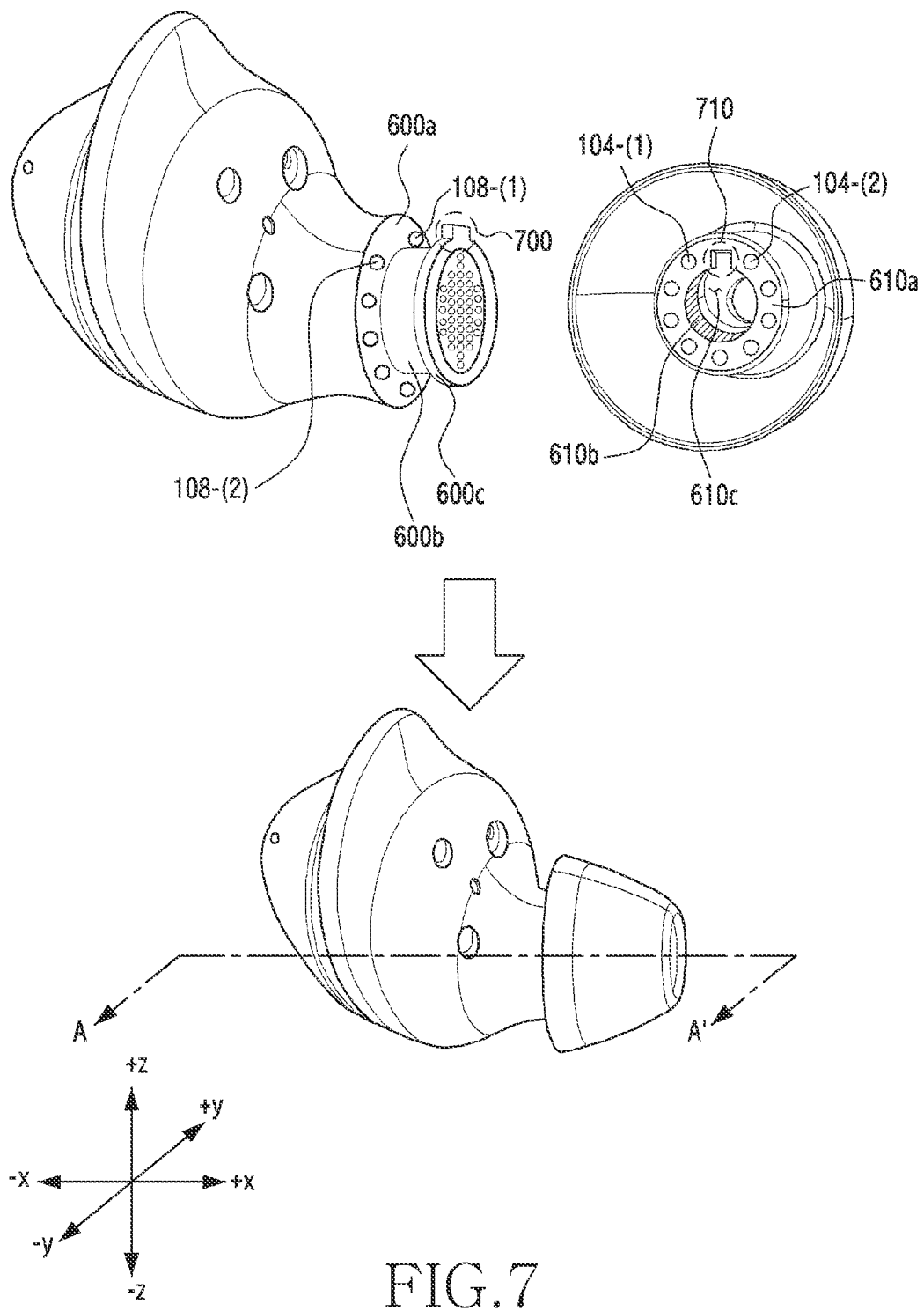
FIG. 7 illustrates a structure of a housing including an embossed protrusion and a buffering member including a recessed groove in an audio output device according to an embodiment of the disclosure.
Figure 8A:
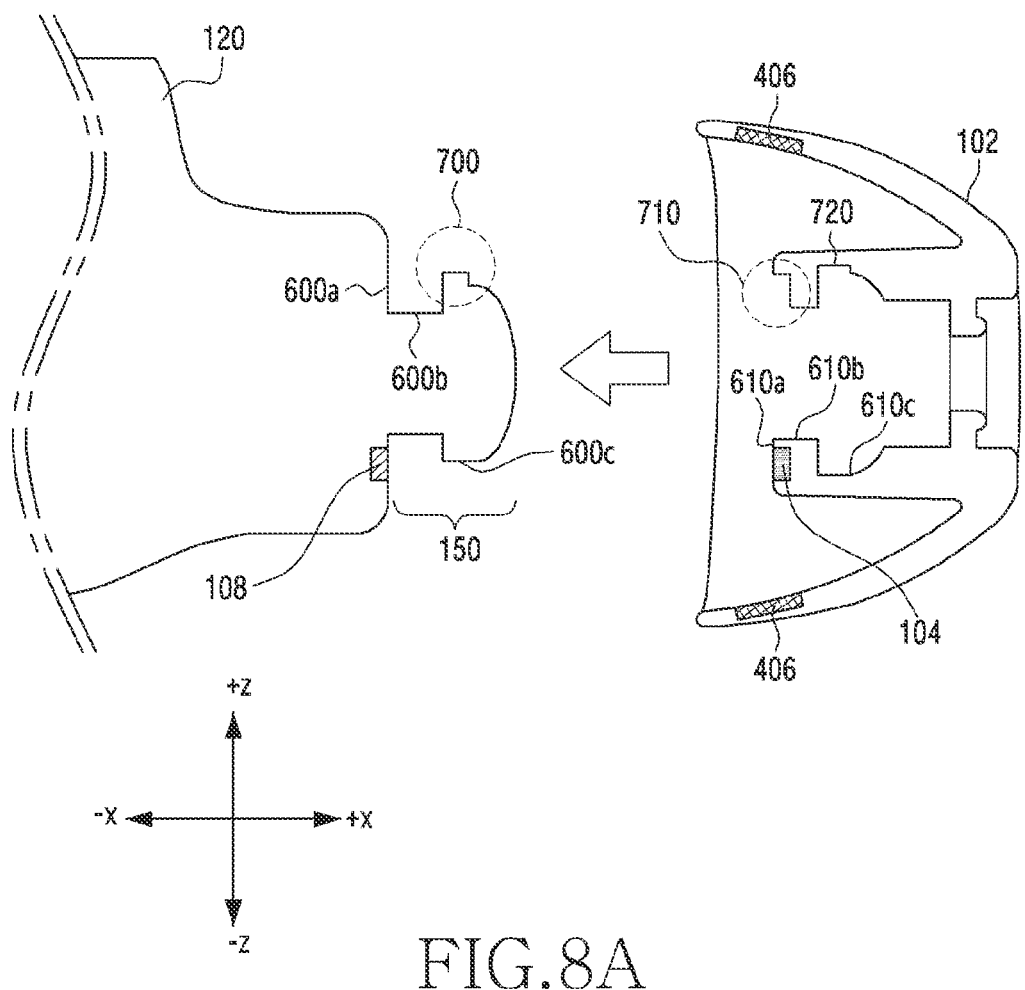
FIG. 8A is a cross-sectional view of an audio output device in a state before the audio output device according to FIG. 7 is coupled according to an embodiment of the disclosure.
Figure 8B:
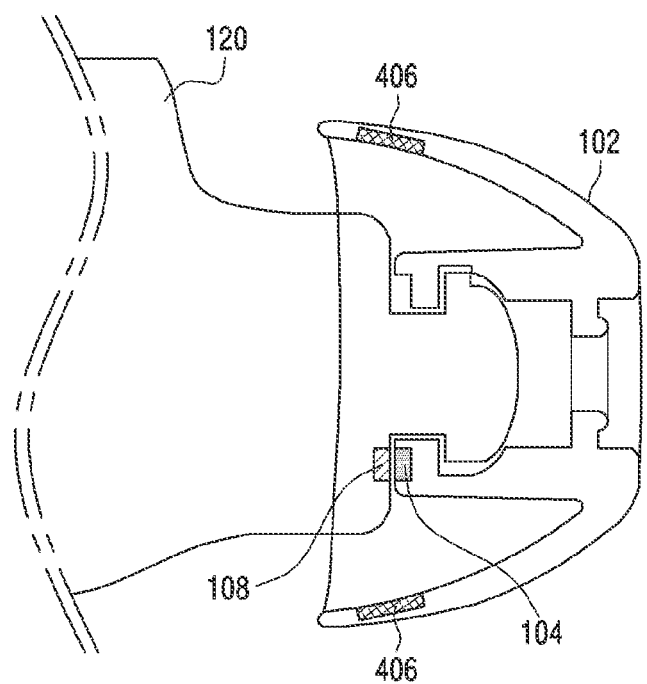
FIG. 8B is a cross-sectional view of an audio output device in a state after the audio output device according to FIG. 7 is coupled according to an embodiment of the disclosure.

FIG. 7 illustrates a structure of a housing including an embossed protrusion and a buffering member including a recessed groove in an audio output device according to an embodiment of the disclosure. FIG. 8A is a cross-sectional view of an audio output device in a state before the audio output device according to FIG. 7 is coupled according to an embodiment of the disclosure. FIG. 8B is a cross-sectional view of an audio output device in a state after the audio output device according to FIG. 7 is coupled, which is taken along the line A-A' and viewed in the −y-axis direction according to an embodiment of the disclosure.

A description that corresponds to the description made in the above embodiments or is the same or similar thereto may be omitted from the description of FIGS. 7, 8A, and 8B. FIG. 8A is a cross-sectional view of an audio output device in the state before the audio output device in FIG. 7 is coupled, which is taken along the line A-A' and viewed in the −y-axis direction.

Referring to FIGS. 7, 8A, and 8B, second terminals 108 including a 2-$1^{st}$ terminal 108-(1) and a 2-$2^{nd}$ terminal 108-(2) may be disposed in a portion of a housing 120 of the audio output device 100. In an embodiment of the disclosure, first terminals 104 including a 1-$1^{st}$ terminal 104-(1) and a 1-$2^{nd}$ terminal 104-(2) may be disposed in a portion of a buffering member 102. Each of the 1-$1^{st}$ terminal 104-(1), the 1-$2^{nd}$ terminal 104-(2), the 2-$1^{st}$ terminal 108-(1), and the 2-$2^{nd}$ terminal 108-(2) may correspond to a terminal performing at least one function among those of a power terminal, a ground (GND) terminal, an LED driver terminal, and a PD terminal. In an embodiment of the disclosure, the 1-$1^{st}$ terminal 104-(1) and the 2-$1^{st}$ terminal 108-(1), and the 1-$2^{nd}$ terminal 104-(2) and the 2-$2^{nd}$ terminal 108-(2) may correspond to terminals that perform the same function. For example, if the 1-$1^{st}$ terminal 104-(1) is a power terminal, the 2-$1^{st}$ terminal 108-(1) may also be a power terminal. If the 1-$2^{nd}$ terminal 104-(2) is a PD terminal, the 2-$2^{nd}$ terminal 108-(2) may also be a PD terminal.

In an embodiment of the disclosure, the housing 120 may include a protrusion (e.g., the protrusion 150 in FIG. 1A) protruding from a portion thereof, and the protrusion 150 may include a first surface 600a, a second surface 600b, and a third surface 600c. In an embodiment of the disclosure, the buffering member 102 may include a connection portion (e.g., the connection portion 412 in FIG. 4B), and the connection portion 412 may include a first surface 610a, a second surface 610b, and a third surface 610c.

In an embodiment of the disclosure, one region of the protrusion 150 may include an embossed protrusion 700, and one region of the connection portion 412, which corresponds to the one region of the protrusion 150, may include a recessed groove 710. For example, the third surface 600c of the protrusion 150 may include an embossed protrusion 700 protruding in the +z direction, and the first surface 610a of the connection portion 412 may include a recessed groove 710 corresponding to the embossed protrusion 700. In an embodiment of the disclosure, the embossed protrusion 700 and the recessed groove 710 may play the role of inducing the housing 120 and the buffering member 102 to be connected in a specific direction. The specific direction may indicate the direction in which at least one first terminal 104 is able to come into contact with at least one second terminal 108 performing the same function. In an embodiment of the disclosure, the connection portion 412 may include an inner groove 720 on the inner side thereof so as to correspond to the embossed protrusion 700. For example, in the case where the housing 120 and the buffering member 102 are connected in a specific direction, the embossed protrusion 700 may come into contact with the recessed groove 710, and may then come into contact with the inner groove 720 as the protrusion 150 is inserted into the connection portion 412.

In an embodiment of the disclosure, an audio output device to be worn in a user's ear may include: a buffering member (e.g., the buffering member 102 in FIG. 2) including a biometric sensor (e.g., the biometric sensor 106 in FIG. 2) and a first terminal (e.g., the first terminal 104 in FIG. 2)

connected to the biometric sensor; a housing (e.g., the housing 120 in FIGS. 1A and 1B) including a portion to which the buffering member is mounted; a second terminal (e.g., the second terminal 108 in FIG. 2) disposed in the portion of the housing and electrically connected to the first terminal of the buffering member; and a control circuit (e.g., the control circuit 110 in FIG. 2) positioned inside the housing and operatively connected to the biometric sensor, the first terminal, and the second terminal, wherein the control circuit may be configured to supply power to the biometric sensor through the second terminal if the first terminal and the second terminal are connected, and to receive at least one piece of biometric signal data obtained from the biometric sensor of the buffering member through the second terminal.

In an embodiment of the disclosure, the buffering member may include a connection portion (e.g., the connection portion 412 in FIG. 4B) formed to be connected to the portion of the housing, and a cover (e.g., the cover 410 in FIG. 4B) formed to extend from the connection portion so as to surround the connection portion, and one region (e.g., the protrusion 150 in FIG. 1A) of the portion of the housing may be formed to protrude and to be inserted into the connection portion of the buffering member.

In an embodiment of the disclosure, the first terminal may be disposed in a portion of the connection portion of the buffering member, and the biometric sensor may be disposed inside the cover of the buffering member.

In an embodiment of the disclosure, the first terminal and the biometric sensor of the buffering member may be connected through at least one of a flexible PCB (FPCB) and a wire.

In an embodiment of the disclosure, the one region of the portion of the housing may include an embossed protrusion (e.g., the embossed protrusion 700 in FIG. 7), and a portion of the connection portion of the buffering member may include a recessed groove (e.g., the recessed groove 710 in FIG. 7) formed to correspond to the embossed protrusion so that the housing and the buffering member may be coupled in one direction.

In an embodiment of the disclosure, the first terminal may include a 1-$1^{st}$ terminal and a 1-$2^{nd}$ terminal, and the second terminal may include a 2-$1^{st}$ terminal corresponding to the 1-$1^{st}$ terminal and a 2-$2^{nd}$ terminal corresponding to the 1-$2^{nd}$ terminal. If the housing and the buffering member are coupled in the one direction, the 1-$1^{st}$ terminal and the 2-$1^{st}$ terminal may come into contact with each other, and the 1-$2^{nd}$ terminal and the 2-$2^{nd}$ terminal may come into contact with each other.

In an embodiment of the disclosure, the biometric sensor may include a first biometric sensor including a first light emitter and a first light receiver disposed adjacent to the first light emitter, and a second biometric sensor including a second light emitter and a second light receiver disposed adjacent to the second light emitter. The control circuit may be configured to receive first biometric signal data obtained from the first biometric sensor, receive second biometric signal data obtained from the second biometric sensor, compare signal quality information of the first biometric signal data with signal quality information of the second biometric signal data, and if the signal quality information of the first biometric signal data has a higher signal quality value than that of the second biometric signal data, select the first biometric signal data.

In an embodiment of the disclosure, the control circuit may be configured to compare the signal quality information, based on a signal-to-noise ratio (SNR) value of the first biometric signal data and an SNR value of the second biometric signal data.

In an embodiment of the disclosure, the buffering member may be formed by silicon molding on at least a portion of the biometric sensor.

In an embodiment of the disclosure, the audio output device may further include a communication module (e.g., the communication module 112 in FIG. 2), and the control circuit may be configured to transmit at least one piece of the obtained biometric signal data to an external electronic device through the communication module.

Figure 9:
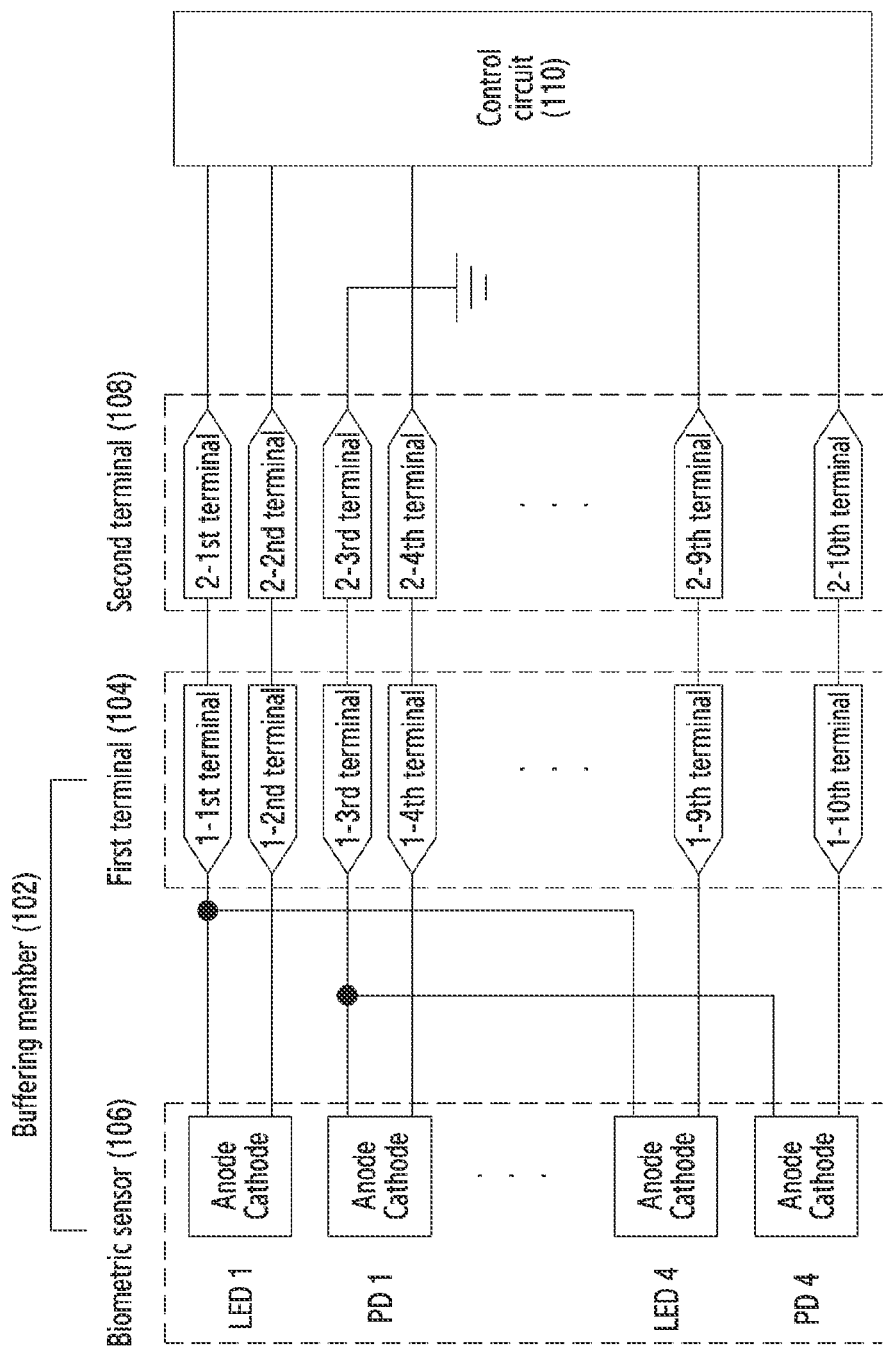
FIG. 9 is a circuit diagram of an audio output device according to an embodiment of the disclosure.

FIG. 9 is a circuit diagram of an audio output device according to an embodiment of the disclosure.

Referring to FIG. 9, an audio output device (e.g., the audio output device 100 in FIG. 2) may include a buffering member 102 including a biometric sensor 106 and first terminals 104, second terminals 108, and a control circuit 110. In an embodiment of the disclosure, the biometric sensor 106 may include one or more light emitters (e.g., LED 1, LED 2, LED 3, and LED 4) and one or more light receivers (e.g., PD 1, PD 2, PD 3, and PD 4). In an embodiment of the disclosure, the light emitters and the light receivers may not correspond to each other one to one. For example, the biometric sensor 106 may include one light emitter and four light receivers.

In an embodiment of the disclosure, at least one light emitter and at least one light receiver of the biometric sensor 106 may be connected to the first terminals 104. In an embodiment of the disclosure, the first terminals 104 may include one or more terminals (e.g., 1-$1^{st}$ terminal to 1-$10^{th}$ terminal). In an embodiment of the disclosure, at least one terminal may correspond to at least one of a power terminal, an LED driver terminal, a ground terminal, and a PD terminal. For example, the 1-$1^{st}$ terminal and the 1-$2^{nd}$ terminal, which are connected to "LED 1" of the biometric sensor 106, may be a power terminal and an LED driver terminal, respectively. The 1-$3^{rd}$ terminal and the 1-$4^{th}$ terminal, which are connected to "PD 1" of the biometric sensor 106, may be a ground terminal and a PD terminal, respectively.

In an embodiment of the disclosure, the control circuit 110 may apply power to at least one light emitter (e.g., "LED 1" to "LED 4") included in the biometric sensor 106 through the 1-$1^{st}$ terminal of the first terminals 104 and the 2-$1^{st}$ terminal of the second terminals 108. In an embodiment of the disclosure, the control circuit 110 may control at least one light emitter included in the biometric sensor 106 through the 1-$2^{nd}$ terminal of the first terminals 104 and the 2-$2^{nd}$ terminal of the second terminals 108. For example, the control circuit 110 may transmit a digital control signal to "LED 1" through the 2-$2^{nd}$ terminal and the 1-$2^{nd}$ terminal. If the digital control signal corresponds to a first value (e.g., "1"), "LED 1" may emit light. If the digital control signal corresponds to a second value (e.g., "0"), "LED 1" may not emit light.

In an embodiment of the disclosure, the 1-$3^{rd}$ terminal of the first terminals 104 and the 2-$3^{rd}$ terminal of the second terminals 108 may be grounded. In an embodiment of the disclosure, the control circuit 110 may receive biometric signal data from the biometric sensor 106 through the 1-$4^{th}$ terminal of the first terminals 104 and the 2-$4^{th}$ terminal of the second terminals 108. For example, at least one light receiver (e.g., "PD 1" to "PD 4") of the biometric sensor 106 may receive an optical signal that is emitted from the light emitter and is then reflected. At least one light receiver may convert the optical signal into an electrical signal, thereby obtaining biometric signal data. The control circuit 110 may receive the biometric signal data converted into the electrical signal through the 1-4$^{th}$ terminal and the 2-4$^{th}$ terminal.

Although FIG. 9 illustrates only an embodiment in which at least one terminal included in the first terminals 104 and the second terminals 108 performs its own function, the disclosure is not limited thereto. In an embodiment of the disclosure, at least one terminal may perform two or more functions among those of a power terminal, an LED driver terminal, and a PD terminal. For example, in the case where the 1-1$^{st}$ terminal and the 2-1$^{st}$ terminal perform the functions of a power terminal and a PD terminal, the control circuit 110 may perform PLC communication with the biometric sensor 106. The control circuit 110 may apply power to the biometric sensor 106 through the 1-1$^{st}$ terminal and the 2-1$^{st}$ terminal, and may receive biometric signal data from the biometric sensor 106. In an embodiment of the disclosure, the first terminals 104 and/or the second terminals 108 may be replaced with a multiplexer (mux) (e.g., 10×10 mux).

Figure 10:
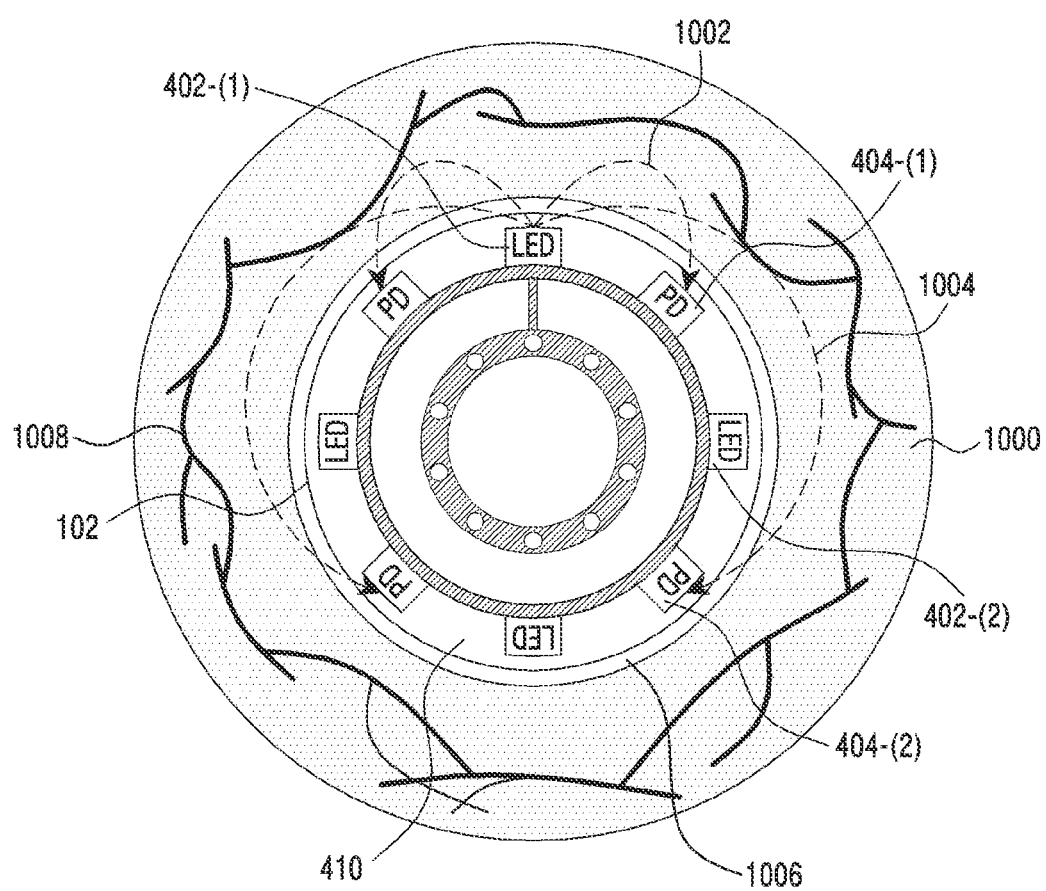
FIG. 10 illustrates optical paths in an audio output device in a state in which a user wears the same according to an embodiment of the disclosure.

FIG. 10 illustrates optical paths in an audio output device in a state in which a user wears the same according to an embodiment of the disclosure.

Referring to FIG. 10, a plurality of biometric sensors including a first biometric sensor and a second biometric sensor may be disposed along the curved surface of a cover 410 of a buffering member 102. In an embodiment of the disclosure, the first biometric sensor may include a first light emitter 402-(1) and a first light receiver 404-(1), and the second biometric sensor may include a second light emitter 402-(2) and a second light receiver 404-(2). The first light emitter 402-(1) and the first light receiver 404-(1) may be disposed to be adjacent to each other, and the second light emitter 402-(2) and the second light receiver 404-(2) may be disposed to be adjacent to each other. The first biometric sensor and the second biometric sensor may be disposed in the order of the first light emitter 402-(1), the first light receiver 404-(1), the second light emitter 402-(2), and the second light receiver 404-(2). The second light receiver 404-(2) may be disposed to be spaced apart from the first light emitter 402-(1).

In an embodiment of the disclosure, a plurality of light receivers may receive signals that are emitted from a plurality of light emitters and are then reflected by the blood vessel 1008 in the body part 1000 (e.g., the ear) of the user. For example, the second light receiver 404-(2) may receive a signal 1004 that is emitted from the first light emitter 402-(1) and is then reflected by the blood vessel 1008, and the biometric sensor 406 may detect a change in the amount of blood flow in the blood vessel 1008.

In an embodiment of the disclosure, in the case where an audio output device (e.g., the audio output device 100 in FIGS. 1A and 1B) is worn in the ear, which is a body part 1000 of the user, an interspace 1006 may be formed between the buffering member 102 and the body part 1000 of the user. However, the interspace 1006 may be formed when the audio output device 100 is loosely worn on the body part 1000 of the user, whereas the interspace 1006 may not be formed when the buffering member 102 comes into close contact with the body part 1000 of the user.

In an embodiment of the disclosure, since a plurality of biometric sensors is disposed along the curved surface, the light receiver may receive a signal that is emitted from a light emitter, which is not adjacent thereto, and is then reflected. For example, the second light receiver 404-(2) may receive a signal 1004 that is emitted from the first light emitter 402-(1) and is then reflected, as well as a signal that is emitted from the second light emitter 402-(2) disposed to be adjacent thereto and is then reflected. The first light receiver 404-(1) may receive a signal 1002 that is emitted from the first light emitter 402-(1) disposed adjacent thereto and is then reflected, and a signal that is emitted from the second light emitter 402-(2) and is then reflected.

Although FIG. 10 illustrates only the optical path of the signal emitted from the first light emitter 402-(1) for the convenience of explanation, the signals emitted from the plurality of light emitters included in the biometric sensor 406 may be transmitted to the light receivers through the same optical path as shown in FIG. 10.

In an embodiment of the disclosure, the control circuit (e.g., the control circuit 110 in FIG. 2) may obtain a plurality of pieces of biometric signal data from the plurality of light receivers. For example, the control circuit 110 may obtain first biometric signal data from the first light receiver 404-(1), and may obtain second biometric signal data received from the second light receiver 404-(2).

In an embodiment of the disclosure, the control circuit 110 may compare signal quality values of the plurality of pieces of obtained biometric signal data. For example, the control circuit 110 may compare a signal-to-noise ratio (SNR) value of the first biometric signal data with an SNR value of the second biometric signal data. If the SNR value of the first biometric signal data is about 5 dB, and if the SNR value of the second biometric signal data is about 15 dB, the control circuit 110 may select the second biometric signal data having the larger SNR value, thereby obtaining biometric data. In an embodiment of the disclosure, the control circuit 110 may compare the plurality of pieces of biometric signal data obtained with reference biometric signal data. For example, the control circuit 110 may measure the similarity between the first biometric signal data and the reference biometric signal data, and may measure the similarity between the second biometric signal data and the reference biometric signal data. If the similarity between the first biometric signal data and the reference biometric signal data is greater than the similarity between the second biometric signal data and the reference biometric signal data, the control circuit 110 may select the first biometric signal data, thereby obtaining biometric data.

Figure 11:
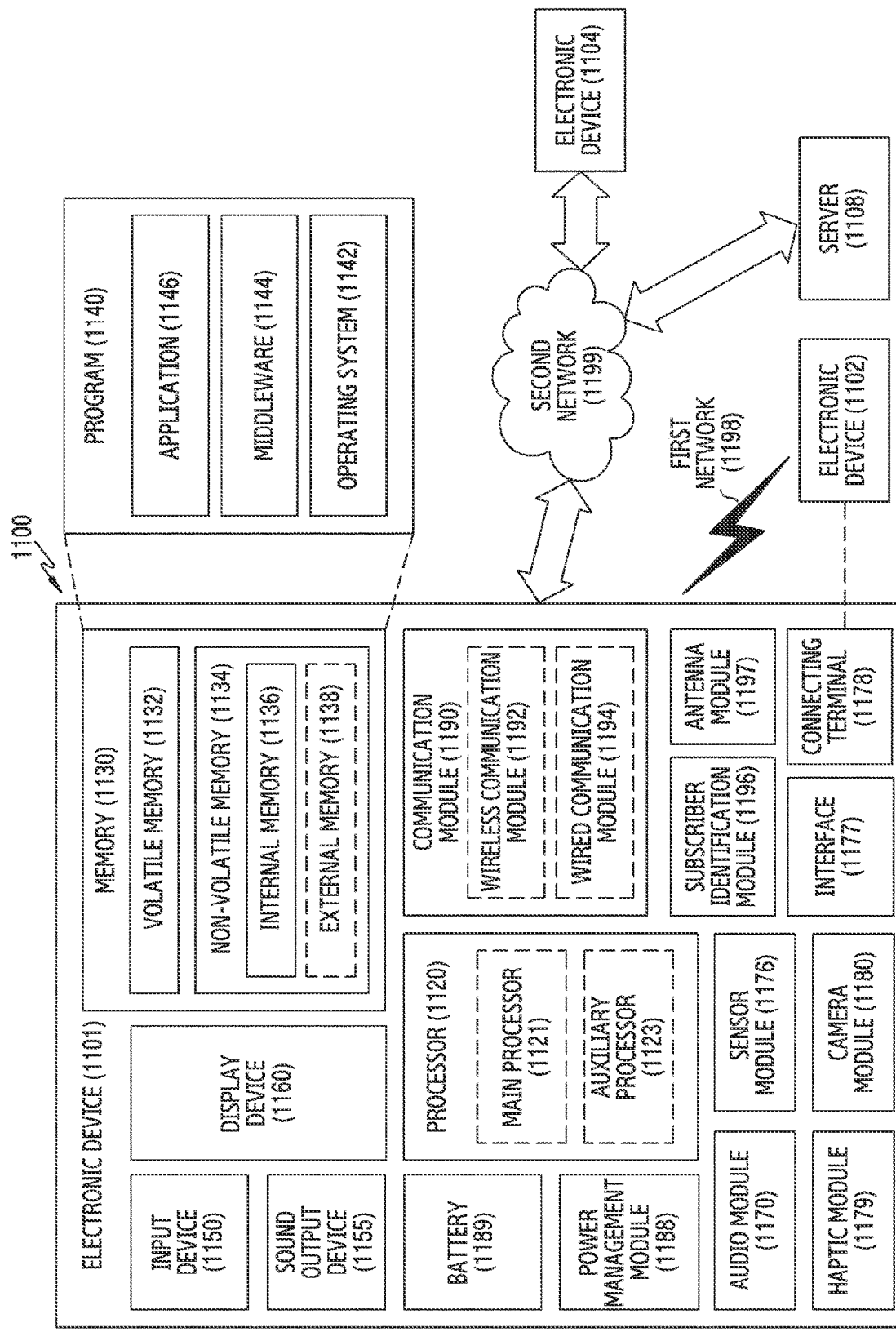
FIG. 11 is a block diagram of an electronic device in a network environment according to an embodiment of the disclosure.

FIG. 11 is a block diagram illustrating an electronic device 1101 in a network environment 1100 according to an embodiment of the disclosure.

Referring to FIG. 11, the electronic device 1101 in the network environment 1100 may communicate with an electronic device 1102 via a first network 1198 (e.g., a short-range wireless communication network), or an electronic device 1104 or a server 1108 via a second network 1199 (e.g., a long-range wireless communication network). According to an embodiment of the disclosure, the electronic device 1101 may communicate with the electronic device 1104 via the server 1108. According to an embodiment of the disclosure, the electronic device 1101 may include a processor 1120, memory 1130, an input device 1150, a sound output device 1155, a display device 1160, an audio module 1170, a sensor module 1176, an interface 1177, a haptic module 1179, a camera module 1180, a power management module 1188, a battery 1189, a communication module 1190, a subscriber identification module (SIM) 1196, or an antenna module 1197. In some embodiments of the disclosure, at least one (e.g., the display device 1160 or the camera module 1180) of the components may be omitted from the electronic device 1101, or one or more other components may be added in the electronic device 1101. In some embodiments of the disclosure, some of the components may be implemented as single integrated circuitry. For example, the sensor module 1176 (e.g., a fingerprint sensor, an iris sensor, or an illuminance sensor) may be implemented as embedded in the display device 1160 (e.g., a display).

The processor 1120 may execute, for example, software (e.g., a program 1140) to control at least one other component (e.g., a hardware or software component) of the electronic device 1101 coupled with the processor 1120, and may perform various data processing or computation. According to an embodiment of the disclosure, as at least part of the data processing or computation, the processor 1120 may load a command or data received from another component (e.g., the sensor module 1176 or the communication module 1190) in volatile memory 1132, process the command or the data stored in the volatile memory 1132, and store resulting data in non-volatile memory 1134. According to an embodiment of the disclosure, the processor 1120 may include a main processor 1121 (e.g., a central processing unit (CPU) or an application processor (AP)), and an auxiliary processor 1123 (e.g., a graphics processing unit (GPU), an image signal processor (ISP), a sensor hub processor, or a communication processor (CP)) that is operable independently from, or in conjunction with, the main processor 1121. Additionally or alternatively, the auxiliary processor 1123 may be adapted to consume less power than the main processor 1121, or to be specific to a specified function. The auxiliary processor 1123 may be implemented as separate from, or as part of the main processor 1121.

The auxiliary processor 1123 may control at least some of functions or states related to at least one component (e.g., the display device 1160, the sensor module 1176, or the communication module 1190) among the components of the electronic device 1101, instead of the main processor 1121 while the main processor 1121 is in an inactive (e.g., sleep) state, or together with the main processor 1121 while the main processor 1121 is in an active state (e.g., executing an application). According to an embodiment of the disclosure, the auxiliary processor 1123 (e.g., an image signal processor or a communication processor) may be implemented as part of another component (e.g., the camera module 1180 or the communication module 1190) functionally related to the auxiliary processor 1123.

The memory 1130 may store various data used by at least one component (e.g., the processor 1120 or the sensor module 1176) of the electronic device 1101. The various data may include, for example, software (e.g., the program 1140) and input data or output data for a command related thereto. The memory 1130 may include the volatile memory 1132 or the non-volatile memory 1134.

The program 1140 may be stored in the memory 1130 as software, and may include, for example, an operating system (OS) 1142, middleware 1144, or an application 1146.

The input device 1150 may receive a command or data to be used by other component (e.g., the processor 1120) of the electronic device 1101, from the outside (e.g., a user) of the electronic device 1101. The input device 1150 may include, for example, a microphone, a mouse, a keyboard, or a digital pen (e.g., a stylus pen).

The sound output device 1155 may output sound signals to the outside of the electronic device 1101. The sound output device 1155 may include, for example, a speaker or a receiver. The speaker may be used for general purposes, such as playing multimedia or playing record, and the receiver may be used for an incoming calls. According to an embodiment of the disclosure, the receiver may be implemented as separate from, or as part of the speaker.

The display device 1160 may visually provide information to the outside (e.g., a user) of the electronic device 1101. The display device 1160 may include, for example, a display, a hologram device, or a projector and control circuitry to control a corresponding one of the display, hologram device, and projector. According to an embodiment of the disclosure, the display device 1160 may include touch circuitry adapted to detect a touch, or sensor circuitry (e.g., a pressure sensor) adapted to measure the intensity of force incurred by the touch.

The audio module 1170 may convert a sound into an electrical signal and vice versa. According to an embodiment of the disclosure, the audio module 1170 may obtain the sound via the input device 1150, or output the sound via the sound output device 1155 or a headphone of an external electronic device (e.g., an electronic device 1102) directly (e.g., wiredly) or wirelessly coupled with the electronic device 1101.

The sensor module 1176 may detect an operational state (e.g., power or temperature) of the electronic device 1101 or an environmental state (e.g., a state of a user) external to the electronic device 1101, and then generate an electrical signal or data value corresponding to the detected state. According to an embodiment of the disclosure, the sensor module 1176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 1177 may support one or more specified protocols to be used for the electronic device 1101 to be coupled with the external electronic device (e.g., the electronic device 1102) directly (e.g., wiredly) or wirelessly. According to an embodiment of the disclosure, the interface 1177 may include, for example, a high definition multimedia interface (HDMI), a universal serial bus (USB) interface, a secure digital (SD) card interface, or an audio interface.

A connecting terminal 1178 may include a connector via which the electronic device 1101 may be physically connected with the external electronic device (e.g., the electronic device 1102). According to an embodiment of the disclosure, the connecting terminal 1178 may include, for example, a HDMI connector, a USB connector, a SD card connector, or an audio connector (e.g., a headphone connector).

The haptic module 1179 may convert an electrical signal into a mechanical stimulus (e.g., a vibration or a movement) or electrical stimulus which may be recognized by a user via his tactile sensation or kinesthetic sensation. According to an embodiment of the disclosure, the haptic module 1179 may include, for example, a motor, a piezoelectric element, or an electric stimulator.

The camera module 1180 may capture a still image or moving images. According to an embodiment of the disclosure, the camera module 1180 may include one or more lenses, image sensors, image signal processors, or flashes.

The power management module 1188 may manage power supplied to the electronic device 1101. According to one embodiment of the disclosure, the power management module 1188 may be implemented as at least part of, for example, a power management integrated circuit (PMIC).

The battery 1189 may supply power to at least one component of the electronic device 1101. According to an embodiment of the disclosure, the battery 1189 may include, for example, a primary cell which is not rechargeable, a secondary cell which is rechargeable, or a fuel cell.

The communication module 1190 may support establishing a direct (e.g., wired) communication channel or a wireless communication channel between the electronic device 1101 and the external electronic device (e.g., the electronic device 1102, the electronic device 1104, or the server 1108) and performing communication via the established communication channel. The communication module 1190 may include one or more communication processors that are operable independently from the processor 1120 (e.g., the application processor (AP)) and supports a direct (e.g., wired) communication or a wireless communication. According to an embodiment of the disclosure, the communication module 1190 may include a wireless communication module 1192 (e.g., a cellular communication module, a short-range wireless communication module, or a global navigation satellite system (GNSS) communication module) or a wired communication module 1194 (e.g., a local area network (LAN) communication module or a power line communication (PLC) module). A corresponding one of these communication modules may communicate with the external electronic device via the first network 1198 (e.g., a short-range communication network, such as Bluetooth™, wireless-fidelity (Wi-Fi) direct, or infrared data association (IrDA)) or the second network 1199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 1192 may identify and authenticate the electronic device 1101 in a communication network, such as the first network 1198 or the second network 1199, using subscriber information (e.g., international mobile subscriber identity (IMSI)) stored in the subscriber identification module 1196.

The antenna module 1197 may transmit or receive a signal or power to or from the outside (e.g., the external electronic device) of the electronic device 1101. According to an embodiment of the disclosure, the antenna module 1197 may include an antenna including a radiating element including a conductive material or a conductive pattern formed in or on a substrate (e.g., PCB). According to an embodiment of the disclosure, the antenna module 1197 may include a plurality of antennas. In such a case, at least one antenna appropriate for a communication scheme used in the communication network, such as the first network 1198 or the second network 1199, may be selected, for example, by the communication module 1190 (e.g., the wireless communication module 1192) from the plurality of antennas. The signal or the power may then be transmitted or received between the communication module 1190 and the external electronic device via the selected at least one antenna. According to an embodiment of the disclosure, another component (e.g., a radio frequency integrated circuit (RFIC)) other than the radiating element may be additionally formed as part of the antenna module 1197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment of the disclosure, commands or data may be transmitted or received between the electronic device 1101 and the external electronic device 1104 via the server 1108 coupled with the second network 1199. Each of the electronic devices 1102 and 1104 may be a device of a same type as, or a different type, from the electronic device 1101. According to an embodiment of the disclosure, all or some of operations to be executed at the electronic device 1101 may be executed at one or more of the external electronic devices 1102, 1104, or 1108. For example, if the electronic device 1101 should perform a function or a service automatically, or in response to a request from a user or another device, the electronic device 1101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 1101. The electronic device 1101 may provide the outcome, with or without further processing of the outcome, as at least part of a reply to the request. To that end, a cloud computing, distributed computing, or client-server computing technology may be used, for example.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment of the disclosure, the module may be implemented in a form of an application-specific integrated circuit (ASIC).

Various embodiments as set forth herein may be implemented as software (e.g., the program 1140) including one or more instructions that are stored in a storage medium (e.g., an internal memory 1136 or an external memory 1138) that is readable by a machine (e.g., the electronic device 1101). For example, a processor (e.g., the processor 1120) of the machine (e.g., the electronic device 1101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment of the disclosure, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments of the disclosure, each component (e.g., a module or a program) of the above-described components may include a single entity or multiple entities. According to various embodiments of the disclosure, one or more of the above-described components may be omitted, or one or more other components may be added. Alternatively or additionally, a plurality of components (e.g., modules or programs) may be integrated into a single component. In such a case, according to various embodiments of the disclosure, the integrated component may still perform one or more functions of each of the plurality of components in the same or similar manner as they are performed by a corresponding one of the plurality of components before the integration. According to various embodiments of the disclosure, operations performed by the module, the program, or another component may be carried out sequentially, in parallel, repeatedly, or heuristically, or one or more of the operations may be executed in a different order or omitted, or one or more other operations may be added.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An audio output device to be worn in an ear of a user, the audio output device comprising:
a buffering member comprising a biometric sensor including a light emitter and a light receiver disposed adjacent to the light emitter and a first terminal connected to the biometric sensor;
a housing comprising a portion to which the buffering member is mounted;
a second terminal disposed in the portion of the housing and electrically connected to the first terminal of the buffering member; and
a control circuit positioned inside the housing and operatively connected to the biometric sensor, the first terminal, and the second terminal,
wherein the control circuit is configured to:
supply power to the biometric sensor through the second terminal if the first terminal and the second terminal are connected, and
receive at least one piece of biometric signal data obtained from the biometric sensor of the buffering member through the second terminal,
wherein the buffering member comprises:
a connection portion formed to be connected to the portion of the housing, and
a cover formed to extend from the connection portion so as to surround the connection portion,
wherein one region of the portion of the housing is formed to protrude and to be inserted into the connection portion of the buffering member
wherein the first terminal is disposed in a portion of the connection portion of the buffering member,
wherein the biometric sensor is implemented of a plurality and is disposed in circular shape inside the cover of the buffering member,
wherein the one region of the portion of the housing comprises an embossed protrusion,
wherein a portion of the connection portion of the buffering member comprises a recessed groove formed to correspond to the embossed protrusion, and
wherein the housing and the buffering member are coupled in one direction,
wherein the first terminal comprises a 1-1st terminal and a 1-2nd terminal,
wherein the second terminal comprises a 2-1st terminal corresponding to the 1-1st terminal and a 2-2nd terminal corresponding to the 1-2nd terminal, and
wherein if the housing and the buffering member are coupled in the one direction, the 1-1st terminal and the 2-1st terminal come into contact with each other, and the 1-2nd terminal and the 2-2nd terminal come into contact with each other.

2. The audio output device of claim 1, wherein the first terminal and the biometric sensor of the buffering member are connected through at least one of a flexible printed circuit board (FPCB) or a wire.

3. The audio output device of claim 1,
wherein the biometric sensor comprises:
a first biometric sensor comprising:
a first light emitter, and
a first light receiver disposed adjacent to the first light emitter, and
a second biometric sensor comprising:
a second light emitter, and
a second light receiver disposed adjacent to the second light emitter, and
wherein the control circuit is configured to:
receive first biometric signal data obtained from the first biometric sensor,
receive second biometric signal data obtained from the second biometric sensor,
compare signal quality information of the first biometric signal data with signal quality information of the second biometric signal data, and if the signal quality information of the first biometric signal data has a higher signal quality value than that of the second biometric signal data, select the first biometric signal data.

4. The audio output device of claim 3, wherein the control circuit is configured to compare the signal quality information, based on a signal-to-noise ratio (SNR) value of the first biometric signal data and an SNR value of the second biometric signal data.

5. The audio output device of claim 1, wherein the buffering member is formed by silicon molding on at least a portion of the biometric sensor.

6. The audio output device of claim 1, further comprising a communication module,
wherein the control circuit is configured to transmit at least one piece of the obtained biometric signal data to an external electronic device through the communication module.

7. A method of operating an audio output device, the method comprising:
if a first terminal disposed in a buffering member and connected to a biometric sensor including a light emitter and a light receiver disposed adjacent to the light emitter, and a second terminal disposed in a portion of a housing to which the buffering member is mounted are connected, supplying power to the biometric sensor through the second terminal; and
receiving at least one piece of biometric signal data obtained from the biometric sensor of the buffering member through the second terminal,
wherein the buffering member comprises:
a connection portion formed to be connected to the portion of the housing, and
a cover formed to extend from the connection portion so as to surround the connection portion, and
wherein one region of the portion of the housing is formed to protrude and to be inserted into the connection portion of the buffering member,
wherein the first terminal is disposed in a portion of the connection portion of the buffering member,
wherein the biometric sensor is implemented of a plurality and is disposed in circular shape inside the cover of the buffering member,
wherein the one region of the portion of the housing comprises an embossed protrusion,
wherein a portion of the connection portion of the buffering member comprises a recessed groove formed to correspond to the embossed protrusion, and
wherein the housing and the buffering member are coupled in one direction
wherein the first terminal comprises a 1-1st terminal and a 1-2nd terminal,
wherein the second terminal comprises a 2-1st terminal corresponding to the 1-1st terminal and a 2-2nd terminal corresponding to the 1-2nd terminal, and
wherein if the housing and the buffering member are coupled in the one direction, the 1-1st terminal and the 2-1st terminal come into contact with each other, and the 1-2nd terminal and the 2-2nd terminal come into contact with each other.

8. The method of claim 7, wherein the first terminal and the biometric sensor of the buffering member are connected through at least one of a flexible printed circuit board (FPCB) or a wire.

9. The method of claim 7, further comprising:
receiving first biometric signal data obtained from a first biometric sensor comprising a first light emitter and a first light receiver disposed adjacent to the first light emitter;
receiving second biometric signal data obtained from a second biometric sensor comprising a second light emitter and a second light receiver disposed adjacent to the second light emitter;
comparing signal quality information of the first biometric signal data with signal quality information of the second biometric signal data; and
if the signal quality information of the first biometric signal data has a higher signal quality value than that of the second biometric signal data, selecting the first biometric signal data.

10. The method of claim 9, further comprising comparing the signal quality information, based on a signal-to-noise ratio (SNR) value of the first biometric signal data and an SNR value of the second biometric signal data.

11. The method of claim 7, wherein the buffering member is formed by silicon molding on at least a portion of the biometric sensor.

12. The method of claim 7, further comprising transmitting at least one piece of the obtained biometric signal data to an external electronic device through a communication module.

* * * * *